United States Patent
Eriksson et al.

(10) Patent No.: US 9,487,579 B2
(45) Date of Patent: Nov. 8, 2016

(54) METHODS AND COMPOSITIONS FOR MODULATION OF BLOOD-NEURAL BARRIER

(71) Applicant: Ludwig Institute for Cancer Research, New York, NY (US)

(72) Inventors: Ulf Eriksson, Stockholm (SE); Linda Fredriksson, Hagersten (SE); Daniel Lawrence, Ann Arbor, MI (US); Enming Su, Ann Arbor, MI (US); Manuel Yepes, Atlanta, GA (US); Dudley Strickland, Brookville, MD (US)

(73) Assignees: LUDWIG INSTITUTE FOR CANCER RESEARCH, New York, NY (US); UNIVERSITY OF MARYLAND, Baltimore, MD (US); THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 149 days.

(21) Appl. No.: 14/282,808

(22) Filed: May 20, 2014

(65) Prior Publication Data

US 2014/0255397 A1 Sep. 11, 2014

Related U.S. Application Data

(62) Division of application No. 13/407,270, filed on Feb. 28, 2012, now Pat. No. 8,765,671, which is a division of application No. 11/736,499, filed on Apr. 17, 2007, now Pat. No. 8,147,828.

(60) Provisional application No. 60/828,506, filed on Oct. 6, 2006, provisional application No. 60/792,318, filed on Apr. 17, 2006.

(51) Int. Cl.
| | | |
|---|---|---|
| C07K 16/18 | (2006.01) | |
| C07K 16/22 | (2006.01) | |
| A61K 39/395 | (2006.01) | |
| C07K 14/475 | (2006.01) | |
| A61K 39/00 | (2006.01) | |

(52) U.S. Cl.
CPC ........... *C07K 16/22* (2013.01); *A61K 39/3955* (2013.01); *A61K 39/39533* (2013.01); *A61K 2039/505* (2013.01); *C07K 2316/96* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 7,375,076 | B2* | 5/2008 | Lawrence | .......... G01N 33/5088 424/143.1 |
| 2002/0164687 | A1* | 11/2002 | Eriksson | ................ C07K 14/49 435/69.1 |
| 2005/0043264 | A1 | 2/2005 | Juang et al. | |
| 2005/0112063 | A1 | 5/2005 | Soker et al. | |
| 2006/0104978 | A1* | 5/2006 | Fredriksson | ........... C07K 14/49 424/146.1 |

FOREIGN PATENT DOCUMENTS

| | | |
|---|---|---|
| WO | 03024478 A1 | 3/2003 |
| WO | 03086178 A2 | 10/2003 |
| WO | 2004050681 A2 | 6/2004 |
| WO | 2005028448 A1 | 3/2005 |
| WO | 2005087954 A2 | 9/2005 |

OTHER PUBLICATIONS

Fang et al. PDGF C is a selective alpha platelet-derived growth factor receptor agonist that is highly expressed in platelet alpha granules and vascular smooth muscle. Arterioscler Thromb Vasc Biol 24: 787-792, 2004.*
Fredricksson et al. Tissue plasminogen activator is a potent activator of PDGF-CC. EMBO J 23: 3793-3802, 2004.*
Fredricksson et al. Structural requirements for activation of latent platelet-derived growth factor CC by tissue plasminogen activator. J Biol Chem 280(29): 26856-26862, 2005.*
Gilbertson et al. Platelet-derived growth factor C (PDGF-C), a novel growth factor that binds to PDGF alpha and beta receptor. J Biol Chem 276(29): 27406-27414, 2001.*
Li et al. PDGF-C is a new protease-activated ligand for the PDGF alpha-receptor. Nature Cell Biol 2: 302-309, 2000.*
Geng et al. STI571 (Gleevec) improves tumor growth delay and surival in irradiated mouse models of glioblastoma. Int J Radiat Oncol Biol Phys64(1): 261-271, 2006; published online Nov. 7, 2005.
Su et al. Activation of PDGF-CC by tissue plasminogen activator impairs blood-brain barrier integrity during ischemic stroke. Nature Medicine 14(7): 731-737, 2008.
"Edema", MayoClinic.com; downloaded from www.mayoclinic.com/health/edema/DS01035 on Apr. 21, 2010; 11 pages.

(Continued)

*Primary Examiner* — Bridget E Bunner
(74) *Attorney, Agent, or Firm* — Fox Rothschild LLP

(57) ABSTRACT

Methods and compositions for modulating blood-neural barrier (BNB) for the treatment of CNS conditions such as edema, and for increased drug delivery efficacy across the BNB. The present invention further relates to improved tPA treatment of ischemic cerebrovascular and related diseases in combination with antagonism of the PDGF signaling pathway. The inventive method and composition is particularly suitable for conjunctive therapy of ischemic stroke using tPA and an anti-PDGF-C antagonist or an anti-PDGFR-α antagonist.

21 Claims, 10 Drawing Sheets

(56) References Cited

OTHER PUBLICATIONS

Ebnoether et al. Cerebral oedema as a possible complication of treatment with imatinib. Lancet 359 1751-1752, 2002.
Kwon et al. Optic disc edema as a possible complication of imatinib mesylate (Gleevec). Jpn J Opthalmol 52: 331-333, 2008.
Reardon et al. Phase II study of imatinib mesylate plus hydroxyurea in adults with recurrent glioblastoma multiforme. J Clin Oncol 23: 9359-9368, 2005.
Breedveld et al. Cancer Res 65(7): 2577-2582, 2005.
Pirollo et al. Targeted delivery of small interfering RNA: approaching effective cancer therapes. Cancer Res 68(5): 1247-1250, 2008.
Vidal et al. Making sense of antisense. Eur J Cancer 41(18): 2812-2818, 2005.
Phillips, A.J. The challenge of gene therapy and DNA delivery. J Pharm Pharmacol 53: 1169-1174, 2001.
Takahasi et al. (Aug. 2006) J. Ocul. Pharmacol. Ther., 22(4):213-218.
Benchenane et al., 2000, Equivocal roles of tissue-type plasminogen activator in stroke-induced injury. TRENDS Neurosci. 27(3): 155-160.

* cited by examiner

METHODS AND COMPOSITIONS FOR MODULATION OF BLOOD-NEURAL BARRIER

CROSS-REFERENCE TO RELATED APPLICATIONS

This application is a Divisional of U.S. patent application Ser. No. 13/407,270, filed Feb. 28, 2012, now U.S. Pat. No. 8,765,671, which is a Divisional of U.S. patent application Ser. No. 11/736,499 filed on Apr. 17, 2007, now U.S. Pat. No. 8,147,828, which claims priority of Provisional Patent Application No. 60/792,318 filed Apr. 17, 2006 and 60/828,506 filed Oct. 6, 2006, all of the disclosures of which are hereby incorporated by reference in their entireties.

STATEMENT OF GOVERNMENT INTEREST

The work leading to this invention was supported in part by the U.S. Government under grants numbered HL50784, HL54710, HL55374, and HL55747, awarded by the National Institutes of Health. The U.S. Government may have certain rights in this invention.

FIELD OF THE INVENTION

The present invention relates to methods and compositions for modulating blood-neural barrier (BNB) for the treatment of CNS conditions such as edema, and for increased drug delivery efficacy across the BNB. The present invention further relates to improved tPA treatment of ischemic cerebrovascular and related diseases in combination with antagonism of the PDGF signaling pathway.

BACKGROUND OF THE INVENTION

The blood-neural barrier (BNB), including blood-brain barrier (BBB) blood-retinal barrier (BRB), and blood-spinal cord barrier, is a barrier that maintains a precisely regulated microenvironment for reliable neuronal activities. The BNB blocks all molecules except those that cross cell membranes by means of lipid solubility (such as oxygen, carbon dioxide, ethanol, and steroid hormones) and those that are allowed in by specific transport systems (such as sugars and some amino acids). In addition, the endothelial cells metabolize certain molecules to prevent their entry into the central nervous system.

The BNB comprises an extensive network of endothelial cells, pericytes, astrocytes and neurons that form functional "neurovascular units." The neurovascular unit is a conserved anatomical structure that is present at all sites where blood vessels meet neural tissues, including brain, retina, and the spinal cord. It is the functional properties of the neurovascular unit that form the blood/brain barrier function in brain, the blood/retina function in the retina, and the blood/spinal cord barrier in the spinal cord. Collectively these barrier functions in various neural tissues are known as the blood/neural barrier. The neurovascular unit is composed of endothelial cells lining the inner surface of the vessel, perivascular pericytes that are tightly attached to the vessel, and an outer sheet of perivascular astrocytes. The presence of tight junctions between endothelial cells and specific BNB transporters (including carrier-mediated, active efflux and receptor-mediated transporters), coupled with a lack of fenestrations, ensure the BNB's function as a selective diffusion barrier.

Astrocytes play a critical role in the development and maintenance, and structure and function of the BNB, as the CNS endothelial cells are surrounded by astrocytic end-foot processes. Astrocytes-endothelial cells interaction influences the BNB in both physiological and pathological conditions. (For review, see Kim et al., 2006, Blood-neural barrier: intercellular communication at glio-vascular interface, J. Biochem. Mol. Biol., 39:339-345).

Because BNB is essential in the regulation of microenvironment of the CNS, breakdown of BNB is closely related with the development and progression of CNS diseases, such as brain edema, stroke, ischemic retinopathies, diabetic retinopathy, Alzheimer's disease, multiple sclerosis, and tumors of the CNS.

Failure of the BNB may be a precipitating event itself or a consequence of another condition. Therefore, there is a need for prevention or inhibition of such breakdowns.

On the other hand, delivery of agents that might otherwise be effective in diagnosis and therapy of CNS disorder is a major challenge for the diagnosis or treatment of most CNS disorders. Substances with a molecular weight higher than 500 daltons generally cannot cross the blood-brain barrier. As a consequence, the delivery of many potentially important diagnostic and therapeutic agents to the CNS is substantially hindered because they do not cross the BNB in adequate amounts.

Various mechanisms for delivering drugs across the BNB have been proposed, such as by disruption of the BBB by osmotic means, biochemically by the use of vasoactive substances such as bradykinin, or even by localized exposure to high intensity focused ultrasound (HIFU). Other strategies to go through the BBB may entail the use of endogenous transport systems, including carrier-mediated transporters such as glucose and amino acid carriers; receptor-mediated transcytosis for insulin or transferrin; and blocking of active efflux transporters such as p-glycoprotein. Strategies for drug delivery behind the BBB include intracerebral implantation and convection-enhanced distribution. It would be highly desirable to have available a method for opening up the BNB and achieve drug delivery via the circulation system.

Edema is the presence of abnormally large amounts of fluid in the intercellular spaces of the tissue which causes tissue swelling. It may be localized or restricted to certain organs, such as edema ascites (peritoneal cavity), hydrothorax (pleural cavity), hydropericardium (pericardial sac), cerebral edema, hydrocephalus, glaucoma, acute pulmonary edema. Edema may also be generalized or systemic, such as anasarca or hydrops, which are massive generalized edema. Local edema may be passive, occurring because of obstruction to vascular or lymphatic drainage from the area, or due to increased vascular permeability. For example, there are several well-known eye diseases that have a component of initial swelling and edema formation, followed by hypoxia of the tissue and undesired induction of angiogenesis. Among these conditions are retinopathies including diabetic retinopathy and maculopathies including wet age-related macula degeneration (AMD). These are major diseases of the eye and millions of patients experience these devastating conditions.

Increased vascular permeability may be due to damage or disruption of the blood vessel endothelium, resulting in excessive transfer of fluids to the extravascular compartment. This type of edema may be observed in patients with cerebral ischemia, head trauma, acute vascular occlusion (i.e., pulmonary embolism), and infection (i.e., sepsis), among others.

More specifically, cerebral edema describes increased water content or maldistribution of water in CNS parenchyma. Cerebral edema is a non-specific reaction to injury that occurs in a wide variety of CNS diseases, including head trauma, subarachnoid hemorrhage and ischemic stroke. There are two basic types of cerebral edema. Vasogenic cerebral edema affects primarily white matter and is due to leaky blood vessels (i.e., a breakdown in the blood brain barrier), where water accumulates in the extracellular space, and total water content of the brain is generally increased. Cytotoxic cerebral edema, on the other hand, affects primarily gray matter and is due to excess water entering the intracellular space. Due to a disturbance of cell membrane function (as in anoxic/ischemic injury) but total water content of the brain is generally not increased.

Cerebral edema associated with pathological conditions often creates intracranial hypertension, and contributes to the morbidity and mortality of patients. It is one of the most common complications associated with ischemic stroke (Garcia et al., 1978, Acta Neuropathol. 43, 85-95; Baker et al., J., 1971, Neuropathol. Exp. Neurol. 30, 668-679).

Few curative therapeutics are available for the treatment of edema. In general, palliative approaches are used in edema treatment, e.g. by decreasing sodium and/or water intake, or increasing sodium and/or water excretion (e.g. by using diuretics or application of local pressure), or via treating the underlying diseases. U.S. patent application Ser. No. 10/849,540, incorporated herein by reference, discloses methods for decreasing vascular permeability via inhibition of tissue-type plasminogen activator (tPA) activity. However, as will become clear from the discussion below, tPA plays an important role in normal physiological functions, and is the only available treatment approved by the FDA for ischemic stroke. Often it is not desirable to generally or globally inhibit tPA activities in patients. Accordingly, an improved edema treatment method is needed.

A stroke or cerebrovascular accident (CVA) occurs when the blood supply to a part of the brain is suddenly interrupted by occlusion of an intra- or extra-cerebral artery (an ischemic stroke, accounting for approximately 90% of strokes), by hemorrhage (a hemorrhagic stroke, accounting for less than 10% of strokes) or other causes. Stroke often induces irreversible neuronal damage, and represents a major health problem in the ever-ageing population of industrialized nations. Each year, over three million people in the U.S. alone suffer from stroke and it is the third leading cause of death and the leading cause of adult morbidity in developed countries. As a consequence, stroke constitutes a considerable socioeconomic burden to society (Benchenane et al., 2004, Trends in Neurosciences 27:155-160).

Since the 1980s, and based on the development of rodent models of experimental cerebral ischemia, many deleterious cellular pathways have been proposed to explain the expansion of ischemic brain lesion, including excitotoxicity, free-radical generation, apoptosis and inflammation (Dirnagl et al., 1999, Pathobiology of ischaemic stroke: an integrated view. Trends Neurosci. 22, 391-3972). To block these deleterious events, several putative neuroprotective molecules such as NMDA antagonists, $Ca^{2+}$ antagonists, free-radical scavengers and caspase inhibitors have been developed and significant beneficial effects have been shown in some or almost all animal models. However, none of these neuroprotective molecules has successfully reached clinically approved application in patients (Kidwell et al., 2001, Trends in acute ischemic stroke trials through the 20th century. Stroke 32, 1349-13593; De Keyser et al., 1999, Clinical trials with neuroprotective drugs in acute ischemic stroke: are we doing the right thing? Trends Neurosci. 22, 535-540). Accordingly, the treatment of ischemic stroke remains one of the most challenging areas in medicine today.

So far, the only treatment approved by the U.S. Food and Drug Administration (FDA) is early reperfusion using the thrombolytic agent tissue-type plasminogen activator (tPA).

tPA is one of the two mammalian serine proteases that cleaves plasminogen into active plasmin. In plasma, the primary function of active plasmin is the digestion of fibrin. Apart from its fibrinolytic function, a growing body of data suggests that tPA also plays a crucial role in the control of the homeostasis of the CNS. In addition to its expression in blood and many peripheral tissues, tPA has been detected in the CNS, and is involved in many physiological functions, such as synaptic outgrowth or neuronal migration during perinatal development. The most common idea is that tPA would facilitate axon elongation by degrading extracellular matrix. Furthermore, accumulating evidence implies roles for tPA in normal neural function in the developed brain and should be considered a neuromodulator in the brain parenchyma. tPA is believed to have relatively broad functions in neural plasticity in various brain areas. For example, it is produced and released by neurons through an exocytotic mechanism, and tPA inhibitors such as the type-1 plasminogen-activator inhibitor (PAI-1) or neuroserpin can block tPA activity in the brain parenchyma. In addition, tPA can be recaptured by astrocytes. Recently, it was also shown that tPA promotes leakage through the blood-brain barrier (Yepes et al., 2003, Tissue-type plasminogen activator induces opening of the blood-brain barrier via the LDL receptor-related protein. J. Clin. Invest. 112, 1533-1540).

Although tPA is clearly beneficial as a thrombolytic agent and has been successfully used to treat myocardial infarction due to clot formation, its use in the treatment of occlusive cerebrovascular diseases remains controversial due to potential deleterious effects. For example, it has been reported that tPA knock-out mice suffered less extensive brain injury and edema following general brain trauma, suggesting that tPA is responsible for the injuries to occur (Mori et al., 2001, Neuroreport. 12:4117-20). In the USA in 1999, up to 80% of stroke patients are ischemic and a large number of them would have benefited from thrombolytic therapy, yet for several reasons less than 5% of stroke patients were treated with tPA. Currently, the recommended window for tPA administration is within 3 hours after occlusion, which suggests that, with time, deleterious effects of tPA in the parenchyma counteract its beneficial effects afforded by reperfusion. tPA only benefits a limited number of the potential patients with ischemic stroke. The limited benefit of tPA seems to be due in part to the unique activities that tPA has in the brain beyond its well established role as a fibrinolytic protease. In particular, tPA has been reported to interact with at least two different cellular receptors expressed in the brain, and these associations have been linked to both neurotoxicity and altered blood-brain-barrier function. Increasing evidence suggests that tPA could also have direct and harmful effects on neurons and glial cells. These recently described effects of tPA present unique challenges for thrombolytic therapy in ischemic stroke.

There is thus also a need for new strategies for lowering some of the side effects and to improve the efficacy of tPA in the treatment of ischemic cerebrovascular diseases and related diseases such as AMD.

SUMMARY OF THE INVENTION

It has now been surprisingly discovered that PDGF platelet derived growth factors (PDGFs), including PDGF-A, PDGF-B and PDGF-C, through their respective receptors and downstream components of the signaling pathways, increase permeability of the blood-neural barrier.

Accordingly, in one embodiment, the present invention provides methods and compositions for modulating permeability of blood-neural barrier in a mammal or higher vertebrate in need thereof, by modulating in a neurovascular unit of the mammal the level or activity of at least one substance selected from the group consisting of PDGF-A, PDGF-B, PDGF-C, PDGFAA, PDGF-AB, PDGF-BB, and PDGF-CC (collectively hereinafter "PDGF"), or their respective receptors PDGFR-α and PDGFR-β (collectively hereinafter "PDGFR"). Specifically, the level or activity of the growth factors or their receptors in a neurovascular unit of the mammal is antagonized for treatment or prevention of edema or related conditions; or alternatively, the level or activity of the growth factors or their receptors may be agonized to increase the opening of the BNB, such that therapeutic agents have increased access to the neural cells or tissues beyond the BNB.

As indicated above, neural edema, such as edema in the brain or spinal cord or other CNS tissue, or edema related to retina, most likely are caused by BNB breach. Accordingly, the present invention provides methods and compositions for treating neural edema via PDGF antagonism. Accordingly, in a preferred embodiment, the present invention provides methods and compositions for the treatment of stroke by decreasing BNB permeability. Although thrombolytic treatments of stroke, e.g. using tPA and Desmoteplase (DSPA) are necessary and beneficial in treating thrombosis, edema remains a side-effect of stroke therapy and would benefit from antagonism of the PDGFs or PDGFRs. In addition, tPA is known to have severe side effects such as neurotoxicity. Accordingly, the methods and compositions of the present invention for PDGF antagonism can be used in combination with the thrombolytic treatments to prevent or ameliorate these side effects. In this regard, the present invention is based on the surprising discovery that PDGF-CC is a downstream effector for tPA activities in vivo. As it is known that tPA increases vascular permeability and may be responsible for edema, the present invention provides, in one embodiment, methods and compositions for treating edema by antagonizing PDGF-C activities or PDGF-C mediated biochemical, physiological or cellular processes. As used in the context of the present invention, the term "PDGF-C antagonist" is broadly defined to include antagonists of PDGF receptors as well as agents that inhibit PDGF-C activities, and its gene transcription, translation, or PDGF-C activation by tPA. PDGF-C antagonists can be used to treat edema by specifically reducing vascular permeability caused by tPA, such as those encountered in pulmonary embolism, cardiovascular diseases, head trauma, infection, other neurological diseases, or other diseases where edema is a significant clinical problem.

In a preferred embodiment, the present invention provides a method of using a substance that specifically inhibits tPA proteolysis/activation of PDGF-CC (e.g. an antibody that specifically binds to the proteolytic site of PDGF-C, or elsewhere on the PDGF-C molecule that causes sterical inhibition of proteolytic cleavage) for the treatment of edema. For example, antibodies and small molecules that bind to PDGF-CC, especially those that specifically recognize the tPA proteolytic site of PDGF-C, can be used to inhibit tPA activation of PDGF-CC.

In yet another embodiment, the present invention provides methods and compositions for improving the treatment, or extending the treatment window, of tPA where thrombolysis is desired, by using PDGF-CC antagonism to counter tPA's undesirable side effects of increasing vascular permeability. Preferably, the present invention provides a combination therapy of ischemic stroke using tPA with a "PDGF-CC antagonist" (as broadly defined above).

Accordingly, the present invention provides a method for treating edema in a patient in need thereof, comprising administering to the patient an effective amount of at least one of a substance that antagonizes PDGF-CC activity, a substance that inhibits PDGF-CC activation, a substance that inhibits PDGF-CC expression, a substance that inhibits PDGFR-α activity. Preferably, the method is used to treat patient suffering from edema ascites, hydrothorax, hydropericardium, cerebral edema, hydrocephalus, glaucoma, acute pulmonary edema, different retinopathies including diabetic retinopathy, and different maculopathies including AMD. In one embodiment, activation of PDGF-CC by tPA is inhibited, preferably by a PDGF-C CUB domain, or an antibody against PDGF-CC, or aptamer that inhibits the binding of tPA to unprocessed PDGF-CC, or a mutant PDGF-C that binds to a PDGF receptor without activating the receptor, or a substance inhibits the binding of PDGF-C to PDGFR-α, or an antibody that binds to PDGF-CC and inhibits tPA proteolysis of PDGF-CC. In a particularly preferred embodiment, the antibody binds specifically to the tPA proteolytic site of PDGF-CC. Suitable substances that inhibit PDGFR-α may also be an anti-PDGFR-α antibody, or a small molecule PDGFR-α antagonist, such as imatinib mesylate. Suitable substances that inhibit PDGFR-α may also be a soluble PDGFR-α that only consists of an extracellular domain, or is a soluble chimeric PDGFR molecule that only consists of an extracellular domain.

The invention also relates to a composition comprising a PDGF-C CUB domain or analog which functions as an inhibitor of PDGF-C proteolysis. Such CUB domain molecules (including allelic variants and hybridizing sequences) bind tPA so that the tPA is sequestered away from the full length PDGF-C and thus cannot bring about the proteolytic cleavage of the full length PDGF-CC protein.

The present invention further provides a method for decreasing vascular permeability in a patient in need thereof, comprising administering to the patient an effective amount of at least one of a substance that antagonizes PDGF-CC activity, a substance that inhibits PDGF-CC activation, a substance that inhibits PDGF-CC expression, a substance that inhibits PDGFR-α activity.

The present invention further provides a method for treating a cerebrovascular disease, comprising administering to a patient in need thereof an effective amount of tissue plasminogen activator (tPA), in combination with an effective amount of at least one of a substance that antagonizes PDGF-CC activity, a substance that inhibits PDGF-CC activation, a substance that inhibits PDGF-CC expression, a substance that inhibits PDGFR-α activity. In preferred embodiments, the PDGF-C antagonist is an anti-PDGF-C antibody, or an anti-PDGFR-α antibody, preferably a monoclonal antibody, more preferably a chimeric, humanized or fully-human antibody. Also, suitable substances that inhibit PDGFR-α may be a soluble PDGFR-α which only consists of an extracellular domain, or is a soluble chimeric PDGFR molecule that only consists of an extracellular domain. The antagonist for the present invention may be administered to the patient in need thereof with tPA concurrently, or sequentially (either before or after tPA administration).

As it is known that the retina is essentially a part of the brain with many similarities regarding cellular composition etc., and as indicated above, there are several well-known eye diseases, such as different retinopathies including diabetic retinopathy, and different macuolopathies including AMD, that have a component of initial swelling and edema formation, followed by hypoxia of the tissue and undesired induction of angiogenesis. Accordingly, in another embodiment, the present invention provides a method for treating ocular diseases that are caused by or have symptoms related to increased vascular permeability. Preferably, the method and compositions of the present invention are used for the treatment of diseases such as diabetic retinopathy or AMD.

A pharmaceutical composition for treating a cerebrovascular disease is also provided by the present invention. The pharmaceutical composition preferably comprises an effective amount of tPA, an anti-PDGF-C antagonist, and a pharmaceutically acceptable excipient. The pharmaceutical composition for reducing vascular permeability preferably comprises an effective amount of tPA, an anti-PDGFR-α antagonist, and a pharmaceutically acceptable excipient.

While the BNB provides the nervous system with a stable physiologic environment and prevents toxins, viruses, and other potentially dangerous molecules from entering, it also prevents therapeutic molecules, including many chemotherapeutic agents that are useful, e.g. in treating tumors, from crossing into the brain, spinal cord, or retina. Thus, many therapies directed at the brain must be delivered directly into the brain cavity, e.g. by an Ommaya reservoir, or administered in elevated dosages to ensure the diffusion of an effective amount across the BBB. It would be highly desirable if these therapeutic agents can be administered via conventional routes such intravenous administration. Accordingly, in another embodiment, the present invention provides a method of increasing BNB permeability or opening via PDGF agonists or PDGF receptor agonists. The present invention further provides method of combination therapy whereby a PDGF agonist or a PDGFR agonist is administered together with a therapeutic agent suitable for treating a condition of the nervous system, such as various types of brain tumors, Alzheimer's, Parkinson's, Multiple Sclerosis.

Accordingly, in one embodiment, the present invention provides a method for modulating permeability of blood-neural barrier in a higher vertebrate animal in need thereof, comprising modulating in a neurovascular unit of the animal the level or activity of at least one substance selected from the group consisting of PDGF-A, PDGF-B, PDGF-C, PDGF-AA, PDGF-BB, PDGF-CC, PDGFR-α and PDGFR-β.

In a preferred embodiment, the level or activity of the at least one substance in a neurovascular unit of the mammal is decreased. Preferably, the method comprises administering to the animal an effective amount of a substance that antagonizes the activity of PDGF-AA, PDGF-BB, or PDGF-CC; a substance that inhibits the activation of PDGF-AA, PDGF-BB, or PDGF-CC; a substance that inhibits the expression of PDGF-A, PDGF-B, or PDGF-C; a substance that inhibits the expression of PDGFR-α or PDGFR-β; a substance that inhibits the binding of a PDGF to its receptor, or a substance that inhibits the activity of PDGFR-α or PDGFR-β. Preferably, the substance is delivered directly in the neurovascular unit of the mammal. Preferably, the level of PDGF-AA, PDGF-BB, or PDGF-CC is decreased. Preferably, a PDGF antagonist is administered to the animal. Preferably, the method comprises administering a PDGFR receptor antagonist to the animal. In one embodiment, the binding of a PDGF with its PDGFR is inhibited, or the expression of PDGF or PDGFR or both is inhibited via a suitable antisense nucleic acid molecule, or a suitable siRNA molecule.

Preferably, the function of PDGF or PDGFR or both are inhibited via a suitable antibody, or a small molecule antagonist.

Preferably, the animal treatable with the method of the present invention is a mammal; more preferably, the animal is a human.

In preferred embodiments, the method is for the treatment of edema. In this context, the substance is preferably a substance that antagonizes PDGF-CC activity, a substance that inhibits PDGF-CC activation, a substance that inhibits PDGF-CC expression, a substance that inhibits PDGFR-α activity, or a substance that inhibits the expression of PDGFR-α.

The method is preferably for treating a patient who suffers from edema ascites, hydrothorax, hydropericardium, cerebral edema, hydrocephalus, glaucoma, acute pulmonary edema, a retinopathy, or a maculopathy, wherein the retinopathy is preferably diabetic retinopathy, or the maculopathy is wet age-related macular degeneration (AMD).

In particular, the method according to the present invention inhibits the activation of PDGF-CC by tPA.

For inhibiting PDGF-CC activation, a PDGF-C CUB domain, a PDGF-CC CUB domain, or an antibody against PDGF-CC, or aptamer that inhibits the binding of tPA to unprocessed PDGF-CC is preferably used. For inhibiting PDGF-CC activation of its receptor, a mutant PDGF-C that binds to a PDGF receptor without activating the receptor, or a substance that inhibits the binding of PDGF-C to PDGFR-α may preferably used, including but not limited to an antibody that binds to PDGF-CC and inhibits tPA proteolysis of PDGF-CC, or an antibody that sterically blocks the biding of PDGF-C with PDGFR-α. An antibody binds specifically to the tPA proteolytic site of PDGF-CC is preferred. An anti-PDGFR-α antibody, or a small molecule PDGFR-α antagonist, such as imatinib mesylate may also be used.

The method of the present invention is preferably used for treating a cerebrovascular disease, the method comprising administering to a patient in need thereof an thrombolytically effective amount of a thrombolytic agent, in combination with an effective amount of at least one of a substance that antagonizes PDGF-CC activity, a substance that inhibits PDGF-CC activation, a substance that inhibits PDGF-CC expression, a substance that inhibits PDGFR-α activity and a substance that inhibits the expression of PDGFR-α. The thrombolytic agent is preferably tissue plasminogen activator (tPA) or desmoteplase (DSPA). Preferably, a PDGF-C antagonist, or a PDGFR-α antagonist, such as a receptor tyrosine kinase inhibitor (e.g. STI-571 or CP-673,451) may be used.

The method of the present invention is particularly suitable for treating ischemic stoke. Specifically, the function of PDGF-CC signaling in the brain of the patient is inhibited, and permeability of blood-brain barrier in the patient is decreased.

Preferably, the PDGF-C antagonist is an anti-PDGF-C antibody, or an anti-PDGFR-α antibody, or a soluble PDGFR-α that only consists of an extracellular domain, or is a soluble chimeric PDGFR molecule that only consists of an extracellular domain. The antibody is preferably a monoclonal antibody, more preferably a chimeric, humanized or fully-human antibody.

The antagonist for the present invention may be administered with the tPA concurrently, or sequentially.

The present invention further provides a pharmaceutical composition for treating a cerebrovascular disease or for reducing vascular permeability, wherein the pharmaceutical composition comprises an effective amount of tPA or DSPA, a PDGF-C antagonist, and a pharmaceutically acceptable excipient. The composition is particularly suitable for treating ischemic stroke.

The present invention further provides a pharmaceutical for the treatment of edema, wherein the pharmaceutical composition comprises an effective amount of a PDGF antagonist or PDGFR antagonist, and a pharmaceutically acceptable excipient. Preferably, the edema is associated with cerebral edema, stroke, ischemic retinopathy, diabetic retinopathy, pulmonary embolism, a cardiovascular disease, head trauma, or infection.

The present invention in an alternative embodiment provides a method for increasing the level or activity PDGF or its receptors in a neurovascular unit of the mammal is increased, whereby vascular permeability of blood-neural barrier (BNB) in the mammal is increased. Preferably, the method comprises administering to the mammal an effective amount of a substance selected from the group of PDGF-AA, PDGF-BB, and PDGF-CC; or an effective amount of a substance that activates PDGF-AA, PDGF-BB, or PDGF-CC; or a substance that increases the expression of PDGF-AA, PDGF-BB, or PDGF-CC. Preferably, the method comprises administering to the mammal an effective amount of a substance selected from the group consisting of activated PDGF-AA, PDGF-BB, and PDGF-CC.

The method of the present invention for increasing PDGF or PDGF level or activity is preferably used for treating a CNS disease, whereby delivering a therapeutic agent to the CNS is facilitated. Preferably, the vascular permeability of the BNB in the patient is increased before the therapeutic agent is delivered; or the vascular permeability of the BNB in the patient is increased concurrently with the delivery of the therapeutic agent. In one embodiment, the therapeutic agent is an anticancer agent.

The method of the present invention for increasing PDGF or PDGF level or activity is preferably used for promoting peripheral nerve regeneration.

In another preferred embodiment, the present invention provides a pharmaceutical composition for treating a CNS disease, comprising an effective amount of PDGF agonist for increasing vascular permeability of the BNB in a patient, a therapeutic agent for the CNS disease, and a pharmaceutically acceptable excipient.

Other advantages and preferred embodiments of the present invention are further described in more detail below.

DETAILED DESCRIPTION OF THE INVENTION

Figure 1:
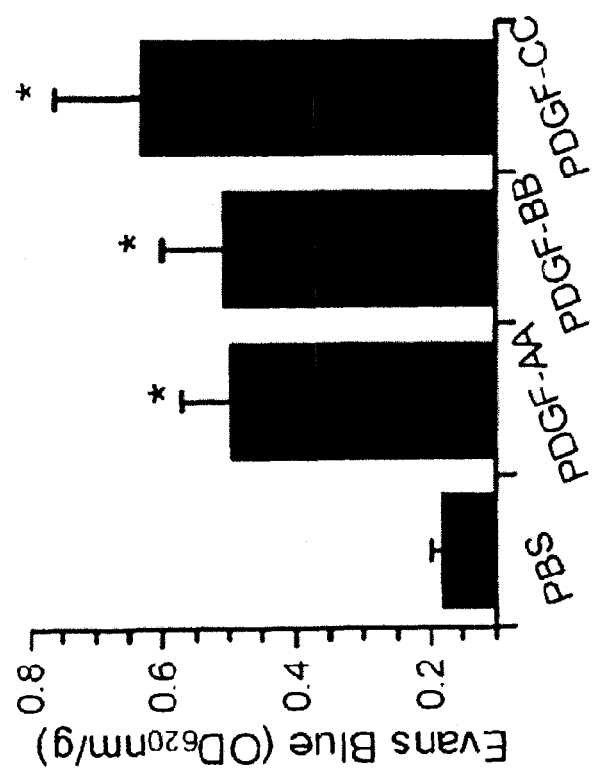
FIG. 1 shows the ability of PDGF-AA, PDGF-BB and PDGF-CC to induce increased vascular permeability following intraventricular injection.

Platelet-derived Growth Factor Platelet-derived growth factors (PDGFs) were discovered more than two decades ago. Today the PDGF family of growth factors consists of five different disulphide-linked dimers built up of four different polypeptide chains encoded by four different genes. These isoforms, PDGF-AA, PDGF-AB, PDGF-BB, PDGF-CC and PDGF-DD, act via two receptor tyrosine kinases, PDGF receptors (PDGFR) α and β. The classic PDGFs, PDGF-AA, PDGF-AB and PDGF-BB, undergo intracellular activation during transport in the exocytic pathway for subsequent secretion, while the novel PDGFs, PDGF-C and PDGF-D, are secreted as latent factors that require activation by extracellular proteases. The classical PDGF polypeptide chains, PDGF-A and PDGF-B, are well studied and they regulate several physiological and pathophysiological processes, mainly using cells of mesenchymal or neuroectodermal origin as their targets. The discovery of two additional ligands for the two PDGF receptors suggests that PDGF-mediated cellular signaling is more complex than previously thought. (Fredriksson et al., 2004, The PDGF family: four gene products form five dimeric isoforms, *Cytokine & Growth Factor Reviews* 15: 197-204). As used in the context of the present invention, the term "PDGF" refers to any of the above five isoforms.

The amino acid sequences of PDGF-AA and BB, and their post translational processing are well-known in the art (see e.g. Johnsson et al. (1984) EMBO J. 3:921-928; U.S. Pat. No. 5,219,759, and U.S. Pat. No. 6,083,910). The mature A-chain consists of a 104 amino acid polypeptide that is derived by proteolytic processing of a 211 amino acid precursor polypeptide. The cDNA encoding the PDGF-B chain has also been described (Nature (1985) 316:748-750). The mature B-chain consists of a 109 amino acid polypeptide that is derived by proteolytic processing of a 241 amino acid precursor polypeptide. The mature A and B chains of PDGF show sequence identity of 51%, with the eight cysteine residues being conserved in each of the chains (Johnsson et al. (1984) EMBO J. 3:921-928). The native protein occurs as the homodimer AA or BB or the heterodimer AB, or a mixture thereof.

PDGF-C is a member of the PDGF/VEGF family of growth factors. PDGF-C, as well as the nucleotide sequence encoding it, are described in U.S. patent application Ser. No. 09/852,209, incorporated herein by reference in its entirety. PDGF-C is one of four known members in the PDGF family of growth factors, which are known mitogens and survival factors for cells of mesenchymal origin. PDGF-C has a unique two-domain structure consisting of an N-terminal CUB and a conserved C-terminal growth factor domain that are separated by a hinge region. PDGF-C is secreted as a latent dimeric factor (PDGF-CC), which undergoes extracellular removal of the CUB domains to become a PDGF receptor a (PDGFR-α) agonist. tPA, a multidomain serine protease tissue plasminogen activator, and a thrombolytic agent used for treatment of acute ischemic stroke, was recently shown to cleave and activate PDGF-CC (see U.S. patent application Ser. No. 10/971,705, incorporated herein by reference).

It has been shown that both the CUB and the growth factor domains of PDGF-C, as well as the kringle-2 domain of tPA, are required for the interaction and cleavage to occur. Specifically, Arg231 in PDGF-C is essential for tPA-mediated proteolysis and that the released "free" CUB domain of PDGF-C can act as a competitive inhibitor of the cleavage reaction.

PDGFs as Modulators of BNB Permeability

In one embodiment, the present invention provides methods of treatment based on PDGF antagonism, i.e. antagonizing PDGF activities, or antagonizing PDGF mediated biochemical, physiological, pathophysiological or cellular processes (e.g. by inhibiting or antagonizing the PDGFR activities, inhibiting PDGF receptor production, or inhibiting the binding of PDGF to a receptor), or by inhibiting PDGF activation, or by inhibiting PDGF production in vivo, either at the gene transcription level, or translation level, or both.

The methods and compositions of the present invention can be used to treat CNS disease such as brain edema, stroke, ischemic retinopathies, diabetic retinopathy, Alzheimer's disease, multiple sclerosis, and tumors of the CNS.

The method of the present invention is especially suitable for treating cerebral edema, pulmonary embolism, cardiovascular diseases, head trauma, infection, neurological diseases, or other diseases where edema is a significant clinical problem. In a particularly preferred embodiment, the present invention is used for the treatment of cerebral edema.

The method of the present invention may also be used for treating localized or restricted edema, such as edema ascites, hydrothorax, hydropericardium, cerebral edema, hydrocephalus, glaucoma, or acute pulmonary edema, as well as generalized or systemic, such as anasarca or hydrops.

Cerebral or brain edemas that may benefit from anti-PDGF receptor alpha or anti-PDGF-CC treatment of the present invention additionally may include but are not limited to ischemic brain edema due to cerebral malaria infection, which kills many children in developing countries (see Penet et al., Imaging experimental cerebral malaria in vivo: significant role of ischemic brain edema. J. Neurosci. 2005; 25:7352-8); brain edema in acute hepatic failure (see Vaquero et al., Brain edema in acute liver failure. A window to the pathogenesis of hepatic encephalopathy. Ann. Hepatol. 2003 2:12-22); edema resulted from brain surgery, which in many aspects resembles brain trauma; edema caused by intracranial tumors (see Papadopoulos et al., Molecular mechanisms of brain tumor edema. Neuroscience. 2004; 129:1011-20; and high altitude cerebral edema (see Hackett and Roach. High altitude cerebral edema. High. Alt. Med. Biol. 2004 5:136-46).

Preferably, PDGF antagonists or a pharmaceutical composition comprising a PDGF antagonist is delivered to the edema sites, for example by direct injection into the cerebrospinal fluid (CSF) in the case of cerebral edema, or via intravascular administration or even intranasal delivery which has been demonstrated to successfully reach the BNB.

PDGF-CC as Down-Stream Effector of tPA for Increased Vascular Permeability

The present inventors discovered that active PDGF-CC, given directly in the CSF, is a potent inducer of opening of BBB, and that both tPA and PDGF-CC are found to be able to open the BBB but that their effects are not synergistic or additive. More importantly, it has been surprisingly discovered that PDGF-C antagonists, if administered together with tPA, dramatically reduces the BNB opening effect of tPA.

Accordingly, the present invention provides for methods of treatment based on PDGF-C antagonism.

The methods and compositions of the present invention can be used to treat edema by specifically reducing vascular permeability caused by tPA. The method of the present invention may be used for treating localized or restricted edema, such as edema ascites, hydrothorax, hydropericardium, cerebral edema, hydrocephalus, glaucoma, or acute pulmonary edema, as well as generalized or systemic, such as anasarca or hydrops. The method of the present invention is especially suitable for treating cerebral edema, pulmonary embolism, cardiovascular diseases, head trauma, infection, neurological diseases, or other diseases where edema is a significant clinical problem. In a particularly preferred embodiment, the present invention is used for the treatment of cerebral edema.

Cerebral or brain edemas that may benefit from anti-PDGF receptor alpha or anti-PDGF-CC treatment of the present invention additionally may include but are not limited to ischemic brain edema due to cerebral malaria infection, which kills many children in developing countries (see Penet et al., Imaging experimental cerebral malaria in vivo: significant role of ischemic brain edema. J. Neurosci. 2005; 25:7352-8); brain edema in acute hepatic failure (see Vaquero et al., Brain edema in acute liver failure. A window to the pathogenesis of hepatic encephalopathy. Ann. Hepatol. 2003 2:12-22); edema resulted from brain surgery, which in many aspects resembles brain trauma; edema caused by intracranial tumors (see Papadopoulos et al., Molecular mechanisms of brain tumor edema. Neuroscience. 2004; 129:1011-20; and high altitude cerebral edema (see Hackett and Roach. High altitude cerebral edema. High. Alt. Med. Biol. 2004 5:136-46).

Preferably, PDGF-C antagonists or a pharmaceutical composition comprising a PDGF-C antagonist is delivered to the edema sites, for example by direct injection into the cerebrospinal fluid (CSF) in the case of cerebral edema, or via intravascular administration or even intranasal delivery which has been demonstrated to successfully reach the BNB, especially BBB.

The therapeutic function of tPA in cerebrovascular diseases, especially ischemic stroke, lies with its thrombolytic activity, while its adverse side effects are due to its effect in increasing vascular permeability and inducing the opening of the blood brain barrier (BBB). U.S. patent application Ser. No. 10/971,705 (Fredriksson et al.) discloses that tPA has the unique capability to proteolytically cleave the CUB domain of the latent PDGF-CC, thereby activating the growth factor. The present inventors have previously demonstrated that tPA is able to open blood brain barrier (BBB) if administered directly into the CSF (see U.S. patent application Ser. No. 10/849,540).

Based on the discovery that PDGF-CC is a downstream effector of tPA, the present invention further provides methods and related compositions for reducing or even eliminating the adverse side effects of tPA for treating ischemic stroke patients, or other patients where cerebral edema is a significant problem, by antagonizing the function of PDGF-CC in the brain when the patient is undergoing tPA treatment.

Because tPA requires PDGF-CC as its down stream effector for BNB opening or increased vascular permeability, antagonizing PDGF-C or the signaling pathway it regulates would counteract the adverse side effects of tPA in ischemic stroke treatment due to undesirable BBB opening, while maintaining the desirable thrombolytic activities.

Because PDGF-CC is not involved in mediating the proteolytic function of tPA, i.e. its serine protease activity in dissolving the blood clot formed as a consequence of stroke, co-administration of a PDGF-C antagonist with tPA would not negatively affect its thrombolytic activities. In particular an antagonist of PDGF-CC combined with tPA can be used to extend the therapeutic window of tPA treatment in ischemic stroke.

DSPA, a member of the plasminogen activator family and is structurally similar to tPA, has been shown to function similarly to tPA with fewer to no neurotoxic side effects. (Reddrop et al., 2005, Vampire bat salivary plasminogen activator (desmoteplase) inhibits tissue-type plasminogen activator-induced potentiation of excitotoxic injury, Stroke: 36:1241-1246). Although DSPA does not have the neurotoxic side effects that tPA has, it does not have any therapeutic effect on edema either. Accordingly, its use as a thrombolytic agent would also benefit from antagonism of the PDGF-C signaling pathway as well.

PDGF Antagonism

Antibodies and Small Molecule Antagonists

As discussed above, any substance that either inhibits a PDGF function directly, or prevents production or its activation is a suitable antagonist for the method and compositions of the present invention. A suitable PDGF antagonist for the present invention may be antibodies or small molecules that inhibit PDGF activation or its binding to PDGFR.

Various methods of producing antibodies with a known antigen are well-known to those ordinarily skilled in the art (see for example, Harlow and Lane, 1988, Antibodies: A Laboratory Manual. Cold Spring Harbor Laboratory Press, Cold Spring Harbor, N.Y.; see also WO 01/25437). In accordance with the present invention, the antibodies or binding fragments thereof may be characterized as those which are capable of specific binding to the PDGF protein or an antigenic fragment thereof, preferably an epitope that is recognized by an antibody when the antibody is administered in vivo. Antibodies can be elicited in an animal host by immunization with a target protein-derived immunogenic component, or can be formed by in vitro immunization (sensitization) of immune cells. The antibodies can also be produced in recombinant systems in which the appropriate cell lines are transformed, transfected, infected or transduced with appropriate antibody-encoding DNA. Alternatively, the antibodies can be constructed by biochemical reconstitution of purified heavy and light chains. In particular, suitable antibodies may be produced by chemical synthesis, by intracellular immunization (i.e., intrabody technology), or preferably, by recombinant expression techniques. Methods of producing antibodies may further include the hybridoma technology well-known in the art.

The antibodies could be polyclonal or monoclonal. The antibodies may be from humans, or from animals other than humans, preferably mammals, such as rat, mouse, guinea pig, rabbit, goat, sheep, and pig. Preferred are mouse monoclonal antibodies and antigen-binding fragments or portions thereof. In addition, chimeric antibodies and hybrid antibodies are embraced by the present invention. Techniques for the production of chimeric antibodies are described in e.g. Morrison et al., 1984, Proc. Natl. Acad. Sci. USA, 81:6851-6855; Neuberger et al., 1984, Nature, 312:604-608;

and Takeda et al., 1985, Nature, 314:452-454. For human therapeutic purposes, humanized, or more preferably, human antibodies are used.

Further, single chain antibodies are also suitable for the present invention (e.g., U.S. Pat. Nos. 5,476,786 and 5,132, 405 to Huston; Huston et al., 1988, Proc. Natl. Acad. Sci. USA, 85:5879-5883; U.S. Pat. No. 4,946,778 to Ladner et al.; Bird, 1988, Science, 242:423-426 and Ward et al., 1989, Nature, 334:544-546). Single chain antibodies are formed by linking the heavy and light immunoglobulin chain fragments of the Fv region via an amino acid bridge, resulting in a single chain polypeptide. Univalent antibodies are also embraced by the present invention.

Many routes of delivery are known to the skilled artisan for delivery of anti-target antibodies. For example, direct injection may be suitable for delivering the antibody to the site of interest. It is also possible to utilize liposomes with antibodies in their membranes to specifically deliver the liposome to the area where target gene expression or function is to be inhibited. These liposomes can be produced such that they contain, in addition to monoclonal antibody, other therapeutic agents, such as those described above, which would then be released at the target site (e.g., Wolff et al., 1984, Biochem. et Biophys. Acta, 802:259).

In one embodiment, the antibodies or small molecules suitable for the present invention target the site of proteolysis in PDGF-C. Such antibodies and small molecules essentially protect the site of PDGF-C proteolysis by binding to it and thereby preventing tPA binding and subsequent cleavage. A peptide sequence, either a monomer or a dimer, which includes the site of PDGF-C proteolysis can be used as an antigen for generation of such antibodies.

The antibodies should preferably recognize the PDGF-C proteolytic site. As Arg231 in PDGF-C is essential for tPA-mediated proteolysis, a preferred target for the antagonist comprises amino acids 231-234 of PDGF-C, especially preferably amino acids 231-235 of PDGF-C. However any antibody or small molecule which binds to any 4 or 5 consecutive amino acids within the range from amino acid 228 to amino acid 238 of PDGF-C could function as an effective antagonist to prevent proteolytic cleavage of PDGF-C. Alternatively, an antibody is also suitable, which, though not specific for the PDGF-C proteolytic site, can sterically block PDGF-C's interaction with the receptor.

As the PDGF-C CUB domain functions as an inhibitor of PDGF-C proteolysis, it is also suitable as a PDGF-C antagonist for the present invention. Such CUB domain molecules (including allelic variants) bind competitively to tPA so that the tPA is sequestered away from the full length PDGF-C and thus cannot bring about the proteolytic cleavage of the full length PDGF-C protein.

Another class of antagonists suitable for the present invention includes substances that inhibit downstream signaling of PDGFR. Antagonists to PDGFR are known and available to those skilled in the art. For example, Axitinib (AG-013736) is a known small molecule inhibitor of the receptor tyrosine kinase with nanomolar potency against PDGFR-α (see e.g. Spano et al., 2006, A phase I study of Axitinib (AG-013736), a potent inhibitor of VEGFRs, in combination with gemcitabine (GEM) in patients (pts) with advanced pancreatic cancer. J. Clin. Oncol. 24:13092). Also, numerous anti-PDGFR-α antibodies are available, including anti-human PDGFR-α polyclonal and monoclonal antibodies that can be obtained commercially from R&D Systems, Inc., Minneapolis, Minn., and IMC-3G3, a fully human IgG1 monoclonal antibody against PDGFR-α, available from Imclone, Inc. Examples of anti-PDGFR antibodies include CDP860, a humanized, engineered Fab' fragment-polyethylene glycol conjugate, which binds to and blocks the activity of PDGFR-β (see e.g. Jayson et al., J. Clin. Oncol. 2005, 23:973-81); and monoclonal antibodies APA5 and APB5, against murine PDGFR-α and PDGFR-β, respectively (see Sano et al. Circulation. 2001, 103:2955-60).

Many small molecules that inhibit receptor tyrosine kinase activities are also known and available to those skilled in the art, and can be used for the present inventive method. These small molecules in general share the same basic mechanism of action, i.e. inhibiting the tyrosine kinase activity of the receptor tyrosine kinases, and many of the small molecule compounds are able to inhibit several tyrosine kinases. For example, imatinib mesylate (also known as Gleevec® or STI-571) is known to at least partially inhibit PDGFR-α. Another PDGFR tyrosine kinase inhibitor, CP-673,451, is described in Roberts et al. Cancer Res. 2005 65:957-66. Other such small molecules include but are not limited to: SU11248 (Mendel et al., In vivo antitumor activity of SU11248, a novel tyrosine kinase inhibitor targeting vascular endothelial growth factor and platelet-derived growth factor receptors: determination of a pharmacokinetic/pharmacodynamic relationship. Clin Cancer Res. 2003 9:327-37; AMG 706 (Polverino et al., AMG 706, an Oral, Multikinase Inhibitor that Selectively Targets Vascular Endothelial Growth Factor, Platelet-Derived Growth Factor, and Kit Receptors, Potently Inhibits Angiogenesis and Induces Regression in Tumor Xenografts. Cancer Res. 2006 66:8715-21); Sorafenib (Adnane et al., Sorafenib (BAY 43-9006, Nexavar®), a Dual-Action Inhibitor That Targets RAF/MEK/ERK Pathway in Tumor Cells and Tyrosine Kinases VEGFR/PDGFR in Tumor Vasculature. Methods Enzymol. 2005; 407:597-612); ABT-869 (Albert et al., Preclinical activity of ABT-869, a multitargeted receptor tyrosine kinase inhibitor. Mol Cancer Ther. 2006, 5:995-1006); PTK787/ZK 222584 (Roboz et al., Phase 1 study of PTK787/ZK 222584, a small molecule tyrosine kinase receptor inhibitor, for the treatment of acute myeloid leukemia and myelodysplastic syndrome. Leukemia. 2006 20:952-7); and BMS-354825 (Chen et al., Potent inhibition of platelet-derived growth factor-induced responses in vascular smooth muscle cells by BMS-354825 (dasatinib). Mol Pharmacol. 2006 69:1527-33).

Mutant PDGF that binds to the receptor but fails to activate the receptor (a dominant negative mutant) may also be used as a PDGF antagonist. Similarly, a soluble PDGFR-α or PDGFR-β that only consists of extracellular domain of this receptor can be used to block PDGF function (a decoy receptor) may be used.

Antibodies used in the invention are preferably chimeric or humanized or fully human antibodies. The antagonists useful in the invention also may include various fragments of immunoglobulin or antibodies known in the art, i.e., Fab, Fab$_2$, F(ab')$_2$, Fv, Fe, Fd, scFvs, etc. A Fab fragment is a multimeric protein consisting of the immunologically active portions of an immunoglobulin heavy chain variable region and an immunoglobulin light chain variable region, covalently coupled together and capable of specifically binding to an antigen. Fab fragments are generated via proteolytic cleavage (with, for example, papain) of an intact immunoglobulin molecule. An Fab$_2$ fragment comprises two joined Fab fragments. When these two fragments are joined by the immunoglobulin hinge region, an F(ab')2 fragment results. An Fv fragment is a multimeric protein consisting of the immunologically active portions of an immunoglobulin heavy chain variable region and an immunoglobulin light chain variable region covalently coupled together and capable of specifically binding to an antigen. A fragment could also be a single chain polypeptide containing only one light chain variable region, or a fragment thereof that contains the three CDRs of the light chain variable region, without an associated heavy chain moiety or, a single chain polypeptides containing only one heavy chain variable region, or a fragment thereof containing the three CDRs of the heavy chain variable region, without an associated light chain moiety; and multi specific antibodies formed from antibody fragments, this has for example been described in U.S. Pat. No. 6,248,516. Fv fragments or single region (domain) fragments are typically generated by expression in host cell lines of the relevant identified regions. These and other immunoglobulin or antibody fragments are within the scope of the invention and are described in standard immunology textbooks such as Paul, Fundamental Immunology or Janeway et al. Immunobiology (cited above). Molecular biology now allows direct synthesis (via expression in cells or chemically) of these fragments, as well as synthesis of combinations thereof.

Antibodies suitable for the present invention may be single chain antibodies or single domain antibodies.

Inhibition of Gene Expression

Several methodologies are known to those ordinarily skilled in the art to inhibit the expression of a gene, either at the transcription level or the translation level, if the identity and sequence of the gene is known. Accordingly, in one embodiment, this invention also provides antisense nucleic acid molecules and compositions comprising such antisense molecules for the inhibition of the expression of PDGF, PDGFR, or a molecule that is known to activate PDGF (e.g. tPA for PDGF-C), preferably at the site where PDGF antagonism is desired, especially at or near the neurovascular unit.

Constitutive expression of antisense RNA in cells has been known to inhibit gene expression, possibly via blockage of translation or prevention of splicing. Interference with splicing allows the use of intron sequences which should be less conserved and therefore result in greater specificity, inhibiting expression of a gene product of one species but not its homologue in another species.

The term antisense component corresponds to an RNA sequence as well as a DNA sequence, which is sufficiently complementary to a particular mRNA molecule, for which the antisense RNA is specific, to cause molecular hybridization between the antisense RNA and the mRNA such that translation of the mRNA is inhibited. Such hybridization can occur under in vivo conditions. This antisense molecule must have sufficient complementarity, about 18-30 nucleotides in length, to the target gene so that the antisense RNA can hybridize to the target gene (or mRNA) and inhibit target gene expression regardless of whether the action is at the level of splicing, transcription, or translation. The antisense components of the present invention may be hybridizable to any of several portions of the target cDNA, including the coding sequence, 3' or 5' untranslated regions, or other intronic sequences, or to target mRNA.

Antisense RNA is delivered to a cell by transformation or transfection via a vector, including retroviral vectors and plasmids, into which has been placed DNA encoding the antisense RNA with the appropriate regulatory sequences including a promoter to result in expression of the antisense RNA in a host cell. In one embodiment, stable transfection and constitutive expression of vectors containing target cDNA fragments in the antisense orientation are achieved, or such expression may be under the control of tissue or development-specific promoters. Delivery can also be achieved by liposomes.

For in vivo therapy, the currently preferred method is direct delivery of antisense oligonucleotides, instead of stable transfection of an antisense cDNA fragment constructed into an expression vector. Antisense oligonucleotides having a size of 15-30 bases in length and with sequences hybridizable to any of several portions of the target cDNA, including the coding sequence, 3' or 5' untranslated regions, or other intronic sequences, or to target mRNA, are preferred. Sequences for the antisense oligonucleotides to target are preferably selected as being the ones that have the most potent antisense effects. Factors that govern a target site for the antisense oligonucleotide sequence include the length of the oligonucleotide, binding affinity, and accessibility of the target sequence. Sequences may be screened in vitro for potency of their antisense activity by measuring inhibition of target protein translation and target related phenotype, e.g., inhibition of cell proliferation in cells in culture. In general it is known that most regions of the RNA (5' and 3' untranslated regions, AUG initiation, coding, splice junctions and introns) can be targeted using antisense oligonucleotides.

The preferred target antisense oligonucleotides are those oligonucleotides which are stable, have a high resistance to nucleases, possess suitable pharmacokinetics to allow them to traffic to target tissue site at non-toxic doses, and have the ability to cross through plasma membranes.

Phosphorothioate antisense oligonucleotides may be used. Modifications of the phosphodiester linkage as well as of the heterocycle or the sugar may provide an increase in efficiency. Phophorothioate is used to modify the phosphodiester linkage. An N3'-P5' phosphoramidate linkage has been described as stabilizing oligonucleotides to nucleases and increasing the binding to RNA. Peptide nucleic acid (PNA) linkage is a complete replacement of the ribose and phosphodiester backbone and is stable to nucleases, increases the binding affinity to RNA, and does not allow cleavage by RNAse H. Its basic structure is also amenable to modifications that may allow its optimization as an antisense component. With respect to modifications of the heterocycle, certain heterocycle modifications have proven to augment antisense effects without interfering with RNAse H activity. An example of such modification is C-5 thiazole modification. Finally, modification of the sugar may also be considered. 2'-O-propyl and 2'-methoxyethoxy ribose modifications stabilize oligonucleotides to nucleases in cell culture and in vivo.

The delivery route will be the one that provides the best antisense effect as measured according to the criteria described above. In vitro and in vivo assays using antisense oligonucleotides have shown that delivery mediated by cationic liposomes, by retroviral vectors and direct delivery are efficient. Another possible delivery mode is targeting using an antibody to cell surface markers for the target cells. Antibody to the target or to its receptor may serve this purpose.

Other nucleic acid sequences which inhibit or interfere with gene expression (e.g., siRNA, ribozymes, and aptamers) can also be used to inhibit or interfere with the activity of RNA or DNA encoding a target protein.

siRNA technology relates to a process of sequence-specific post-transcriptional gene repression which can occur in eukaryotic cells. In general, this process involves degradation of an mRNA of a particular sequence induced by double-stranded RNA (dsRNA) that is homologous to that sequence. For example, the expression of a long dsRNA corresponding to the sequence of a particular single-stranded mRNA (ss mRNA) will labilize that message, thereby "interfering" with expression of the corresponding gene. Accordingly, any selected gene may be repressed by introducing a dsRNA which corresponds to all or a substantial part of the mRNA for that gene. It appears that when a long dsRNA is expressed, it is initially processed by a ribonuclease III into shorter dsRNA oligonucleotides of as few as 21 to 22 base pairs in length. Accordingly, siRNA may be effected by introduction or expression of relatively short homologous dsRNAs. Indeed the use of relatively short homologous dsRNAs may have certain advantages as discussed below.

Mammalian cells have at least two pathways that are affected by double-stranded RNA (dsRNA). In the siRNA (sequence-specific) pathway, the initiating dsRNA is first broken into short interfering (si) RNAs, as described above. The siRNAs have sense and antisense strands of about 21 nucleotides that form approximately 19 nucleotide siRNAs with overhangs of two nucleotides at each 3' end. Short interfering RNAs are thought to provide the sequence information that allows a specific messenger RNA to be targeted for degradation. In contrast, the nonspecific pathway is triggered by dsRNA of any sequence, as long as it is at least about 30 base pairs in length.

The nonspecific effects occur because dsRNA activates two enzymes: PKR, which in its active form phosphorylates the translation initiation factor eIF2 to shut down all protein synthesis, and 2', 5' oligoadenylate synthetase (2', 5'-AS), which synthesizes a molecule that activates RNase L, a nonspecific enzyme that targets all mRNAs. The nonspecific pathway may represent a host response to stress or viral infection, and, in general, the effects of the nonspecific pathway are preferably minimized. Significantly, longer dsRNAs appear to be required to induce the nonspecific pathway and, accordingly, dsRNAs shorter than about 30 bases pairs are preferred to effect gene repression by RNAi (see Hunter et al., 1975, J. Biol. Chem. 250:409-17; Manche et al., 1992, Mol. Cell. Biol. 12:5239-48; Minks et al., 1979, J. Biol. Chem. 254:10180-3; and Elbashir et al., 2001, Nature 411:494-8). siRNA has proven to be an effective means of decreasing gene expression in a variety of cell types including HeLa cells, NIH/3T3 cells, COS cells, 293 cells and BHK-21 cells, and typically decreases expression of a gene to lower levels than that achieved using antisense techniques and, indeed, frequently eliminates expression entirely (see Bass, 2001, Nature 411:428-9). In mammalian cells, siRNAs are effective at concentrations that are several orders of magnitude below the concentrations typically used in antisense experiments (Elbashir et al., 2001, Nature 411:494-8).

The double stranded oligonucleotides used to effect RNAi are preferably less than 30 base pairs in length and, more preferably, comprise about 25, 24, 23, 22, 21, 20, 19, 18 or 17 base pairs of ribonucleic acid. Optionally the dsRNA oligonucleotides may include 3' overhang ends. Exemplary 2-nucleotide 3' overhangs may be composed of ribonucleotide residues of any type and may even be composed of 2'-deoxythymidine resides, which lowers the cost of RNA synthesis and may enhance nuclease resistance of siRNAs in the cell culture medium and within transfected cells (see Elbashi et al., 2001, Nature 411:494-8).

Longer dsRNAs of 50, 75, 100 or even 500 base pairs or more may also be utilized in certain embodiments of the invention. Exemplary concentrations of dsRNAs for effecting RNAi are about 0.05 nM, 0.1 nM, 0.5 nM, 1.0 nM, 1.5 nM, 25 nM or 100 nM, although other concentrations may be utilized depending upon the nature of the cells treated, the gene target and other factors readily discernable to the skilled artisan.

Exemplary dsRNAs may be synthesized chemically or produced in vitro or in vivo using appropriate expression vectors. Exemplary synthetic RNAs include 21 nucleotide RNAs chemically synthesized using methods known in the art. Synthetic oligonucleotides are preferably deprotected and gel-purified using methods known in the art (see e.g. Elbashir et al., 2001, Genes Dev. 15:188-200). Longer RNAs may be transcribed from promoters, such as T7 RNA polymerase promoters, known in the art. A single RNA target, placed in both possible orientations downstream of an in vitro promoter, will transcribe both strands of the target to create a dsRNA oligonucleotide of the desired target sequence. Any of the above RNA species will be designed to include a portion of nucleic acid sequence represented in a target nucleic acid.

The specific sequence utilized in design of the oligonucleotides may be any contiguous sequence of nucleotides contained within the expressed gene message of the target. Programs and algorithms, known in the art, may be used to select appropriate target sequences. In addition, optimal sequences may be selected utilizing programs designed to predict the secondary structure of a specified single stranded nucleic acid sequence and allowing selection of those sequences likely to occur in exposed single stranded regions of a folded mRNA. Methods and compositions for designing appropriate oligonucleotides may be found, for example, in U.S. Pat. No. 6,251,588, the contents of which are incorporated herein by reference.

Although mRNAs are generally thought of as linear molecules containing the information for directing protein synthesis within the sequence of ribonucleotides, most mRNAs have been shown to contain a number of secondary and tertiary structures. Secondary structural elements in RNA are formed largely by Watson-Crick type interactions between different regions of the same RNA molecule. Important secondary structural elements include intramolecular double stranded regions, hairpin loops, bulges in duplex RNA and internal loops. Tertiary structural elements are formed when secondary structural elements come in contact with each other or with single stranded regions to produce a more complex three dimensional structure. A number of researchers have measured the binding energies of a large number of RNA duplex structures and have derived a set of rules which can be used to predict the secondary structure of RNA (see e.g. Jaeger et al., 1989, Proc. Natl. Acad. Sci. USA 86:7706; and Turner et al., 1988, Annu. Rev. Biophys. Biophys. Chem. 17:167). The rules are useful in identification of RNA structural elements and, in particular, for identifying single stranded RNA regions which may represent preferred segments of the mRNA to target for siRNA, ribozyme or antisense technologies. Accordingly, preferred segments of the mRNA target can be identified for design of the siRNA mediating dsRNA oligonucleotides as well as for design of appropriate ribozyme and hammerhead ribozyme compositions of the invention (see below).

The dsRNA oligonucleotides may be introduced into the cell by transfection with a heterologous target gene using carrier compositions such as liposomes, which are known in the art—e.g. Lipofectamine 2000 (Life Technologies) as described by the manufacturer for adherent cell lines. Transfection of dsRNA oligonucleotides for targeting endogenous genes may be carried out using Oligofectamine (Life Technologies). Transfection efficiency may be checked using fluorescence microscopy for mammalian cell lines after co-transfection of hGFP-encoding pAD3 (Kehlenback et al., 1998, J. Cell Biol. 141:863-74). The effectiveness of the siRNA may be assessed by any of a number of assays following introduction of the dsRNAs. These include Western blot analysis using antibodies which recognize the target gene product following sufficient time for turnover of the endogenous pool after new protein synthesis is repressed, reverse transcriptase polymerase chain reaction and Northern blot analysis to determine the level of existing target mRNA.

Further compositions, methods and applications of siRNA technology are provided in U.S. Pat. Nos. 6,278,039, 5,723, 750 and 5,244,805, which are incorporated herein by reference.

Ribozymes are enzymatic RNA molecules capable of catalyzing specific cleavage of RNA. (For a review, see Rossi, 1994, Current Biology 4:469-471). The mechanism of ribozyme action involves sequence specific hybridization of the ribozyme molecule to complementary target RNA, followed by an endonucleolytic cleavage event. The composition of ribozyme molecules preferably includes one or more sequences complementary to a target mRNA, and the well known catalytic sequence responsible for mRNA cleavage or a functionally equivalent sequence (see, e.g., U.S. Pat. No. 5,093,246, which is incorporated herein by reference in its entirety). Ribozyme molecules designed to catalytically cleave target mRNA transcripts can also be used to prevent translation of subject target mRNAs.

While ribozymes that cleave mRNA at site-specific recognition sequences can be used to destroy target mRNAs, the use of hammerhead ribozymes is preferred. Hammerhead ribozymes cleave mRNAs at locations dictated by flanking regions that form complementary base pairs with the target mRNA. Preferably, the target mRNA has the following sequence of two bases: 5'-UG-3'. The construction and production of hammerhead ribozymes is well known in the art and is described more fully in Haseloff and Gerlach, 1988, Nature 334:585-591; and PCT Application. No. WO89/05852, the contents of which are incorporated herein by reference. Hammerhead ribozyme sequences can be embedded in a stable RNA such as a transfer RNA (tRNA) to increase cleavage efficiency in vivo (Perriman et al., 1995, Proc. Natl. Acad. Sci. USA, 92:6175-79; de Feyter, and Gaudron, Methods in Molecular Biology, Vol. 74, Chapter 43, "Expressing Ribozymes in Plants", Edited by Turner, P. C, Humana Press Inc., Totowa, N.J.). In particular, RNA polymerase III-mediated expression of tRNA fusion ribozymes are well known in the art (see Kawasaki et al., 1998, Nature 393:284-9; Kuwabara et al., 1998, Nature Biotechnol. 16:961-5; and Kuwabara et al., 1998, Mol. Cell 2:617-27; Koseki et al., 1999, J. Virol 73:1868-77; Kuwabara et al., 1999, Proc. Natl. Acad. Sci. USA, 96:1886-91; Tanabe et al., 2000, Nature 406:473-4). There are typically a number of potential hammerhead ribozyme cleavage sites within a given target cDNA sequence. Preferably the ribozyme is engineered so that the cleavage recognition site is located near the 5' end of the target mRNA- to increase efficiency and minimize the intracellular accumulation of non-functional mRNA transcripts. Furthermore, the use of any cleavage recognition site located in the target sequence encoding different portions of the target mRNA would allow the selective targeting of one or the other target genes.

Gene targeting ribozymes necessarily contain a hybridizing region complementary to two regions, each of at least 5 and preferably each 6, 7, 8, 9, 10, 11, 12, 13, 14, 15, 16, 17, 18, 19 or 20 contiguous nucleotides in length of a target mRNA. In addition, ribozymes possess highly specific endoribonuclease activity, which autocatalytically cleaves the target sense mRNA.

The ribozymes of the present invention also include RNA endoribonucleases ("Cech-type ribozymes") such as the one which occurs naturally in *Tetrahymena thermophila* (known as the IVS, or L-19 IVS RNA) and which has been extensively described in Zaug, et al., 1984, Science, 224:574-578; Zaug, et al., 1986, Science 231:470-475; Zaug, et al., 1986, Nature 324:429-433; published International patent application No. WO88/04300; and Been, et al., 1986, Cell 47:207-216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in a target gene or nucleic acid sequence.

Ribozymes can be composed of modified oligonucleotides (e.g., for improved stability, targeting, etc.) and should be delivered to cells which express the target gene in vivo. A preferred method of delivery involves using a DNA construct "encoding" the ribozyme under the control of a strong constitutive promoter, so that transfected cells will produce sufficient quantities of the ribozyme to destroy endogenous target messages and inhibit translation. Because ribozymes, unlike antisense molecules, are catalytic, a lower intracellular concentration is required for efficiency.

In certain embodiments, a ribozyme may be designed by first identifying a sequence portion sufficient to cause effective knockdown by RNAi. The same sequence portion may then be incorporated into a ribozyme. In this aspect of the invention, the gene-targeting portions of the ribozyme or siRNA are substantially the same sequence of at least 5 and preferably 6, 7, 8, 9, 10, 11, 12, 13, 14, 15, 16, 17, 18, 19 or 20 or more contiguous nucleotides of a target nucleic acid.

In a long target RNA chain, significant numbers of target sites are not accessible to the ribozyme because they are hidden within secondary or tertiary structures (Birikh et al., 1997, Eur. J. Biochem. 245:1-16). To overcome the problem of target RNA accessibility, computer generated predictions of secondary structure are typically used to identify targets that are most likely to be single-stranded or have an "open" configuration (see Jaeger et al., 1989, Methods Enzymol. 183:281-306). Other approaches utilize a systematic approach to predicting secondary structure which involves assessing a huge number of candidate hybridizing oligonucleotides molecules (see Milner et al., 1997, Nat. Biotechnol. 15: 537-41; and Patzel and Sczakiel, 1998, Nat. Biotechnol. 16:64-8). Additionally, U.S. Pat. No. 6,251,588, the contents of which are herein incorporated by reference, describes methods for evaluating oligonucleotide probe sequences so as to predict the potential for hybridization to a target nucleic acid sequence. The method of the invention provides for the use of such methods to select preferred segments of a target mRNA sequence that are predicted to be single-stranded and, further, for the opportunistic utilization of the same or substantially identical target mRNA sequence, preferably comprising about 10-20 consecutive nucleotides of the target mRNA, in the design of both the siRNA oligonucleotides and ribozymes of the invention.

Another class of substances that serve as PDGF antagonists are aptamers. Aptamers are chemically synthesized (usually short) strands of oligonucleotides (DNA or RNA) that can adopt highly specific three-dimensional conformations. Aptamers are designed to have appropriate binding affinities and specificities towards certain target molecules, and can be selected via the Systematic Evolution of Ligands by Exponential Enrichments (SELEX) process. SELEX is a method of the in vitro evolution of nucleic acid molecules with highly specific binding to target molecules and is described in e.g. U.S. Pat. Nos. 5,475,096, 5,580,737, 5,567,588, 5,707,796, 5,763,177, 6,011,577, and 6,699,843, incorporated herein by reference in their entirety. An aptamer has a unique sequence, has the property of binding specifically to a desired target compound, and is a specific ligand of a given target compound or molecule. The SELEX process is based on the capacity of nucleic acids for forming a variety of two- and three-dimensional structures, as well as the chemical versatility available within the nucleotide monomers to act as ligands (form specific binding pairs) with virtually any chemical compound, whether monomeric or polymeric, including other nucleic acid molecules and polypeptides. Molecules of any size or composition can serve as targets. Because the specific tPA proteolysis site on PDGF-C and PDGF-CC is known, screening using SELEX process for aptamers that act on PDGF, PDGFR, or a protease that is known to activate a PDGF (e.g. tPA for PDGF-C), would allow the identification of aptamer that can function as a PDGF antagonist. The SELEX method involves selection from a mixture of candidate oligonucleotides and step-wise iterations of binding, partitioning and amplification, using the same general selection scheme, to achieve desired binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand enriched mixture of nucleic acids, then reiterating the steps of binding, partitioning, dissociating and amplifying through as many cycles as desired to yield highly specific high affinity nucleic acid ligands to the target molecule.

Alternatively, target gene expression can be reduced by targeting deoxyribonucleotide sequences complementary to the regulatory region of the gene (i.e., the promoter and/or enhancers) to form triple helical structures that prevent transcription of the gene in target cells in the body. (See generally, Helene, C., 1991, Anticancer Drug Des., 6:569-84; Helene, C., et al., 1992, Ann. N.Y. Acad. Sci., 660:27-36; and Maher, L. J., 1992, Bioassays 14:807-15).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

A further aspect of the invention relates to the use of DNA enzymes to inhibit expression of target gene. DNA enzymes incorporate some of the mechanistic features of both antisense and ribozyme technologies. DNA enzymes are designed so that they recognize a particular target nucleic acid sequence, much like an antisense oligonucleotide. They are, however, catalytic and specifically cleave the target nucleic acid.

There are currently two basic types of DNA enzymes, both of which were identified by Santoro and Joyce (see, for example, U.S. Pat. No. 6,110,462). The 10-23 DNA enzyme comprises a loop structure which connect two arms. The two arms provide specificity by recognizing the particular target nucleic acid sequence while the loop structure provides catalytic function under physiological conditions.

Briefly, to design an ideal DNA enzyme that specifically recognizes and cleaves a target nucleic acid, one of skill in the art must first identify the unique target sequence. This can be done using the same approach as outlined for antisense oligonucleotides. Preferably, the unique or substantially sequence is a G/C rich of approximately 18 to 22 nucleotides. High G/C content helps insure a stronger interaction between the DNA enzyme and the target sequence.

When synthesizing the DNA enzyme, the specific antisense recognition sequence that will target the enzyme to the message is divided so that it comprises the two arms of the DNA enzyme, and the DNA enzyme loop is placed between the two specific arms.

Methods of making and administering DNA enzymes can be found, for example, in U.S. Pat. No. 6,110,462. Similarly, methods of delivery of DNA ribozymes in vitro or in vivo are similar to methods of delivery of RNA ribozyme, as outlined in detail above. Additionally, one of skill in the art will recognize that, like antisense oligonucleotide, DNA enzymes can be optionally modified to improve stability and improve resistance to degradation.

Delivery Routes

The present method delivers PDGF antagonist to the subject via any approach that effectively will reach the tissue where the activity of PDGF is desired to be inhibited, especially at or near the neurovascular unit, using any mode of administration that is medically acceptable. Pharmaceutical compositions containing the PDGF antagonist in combination with a pharmaceutically acceptable carrier may be administered parenterally, intrathecally, intracisternally, intravaginally, topically (as by powders, ointments, drops or transdermal patch), bucally, or as an oral or nasal spray (intranasally). The term "parenteral" includes subcutaneous, intravenous, intramuscular, or infusion. Other routes of administration include per oz, intra-cranially or intrathecally (delivery directly into the spinal cord).

Preferably, the antagonists of the invention can be administered parenterally by injection or by gradual perfusion over time. The antagonists can be administered intravenously, intraperitoneally, intramuscularly, subcutaneously, intracavity, or transdermally. The antagonists of the invention may also be administered per oz.

When the pharmaceutical composition of the present invention is administered to the eye, it may be formulated for intraocular injection or topical application, such as by an ophthalmic solution. Topical ophthalmic preparations, for example, ocular drops, gels, or creams, are preferable because of the ease of application, ease of dose delivery, and fewer systemic side effects. Intraocular injection may be desirable or necessary, for example, for conditions in which topical administration is either not advised or is inadequate, for patients who have difficulty self-administering medications, etc. Intraocular injection may be into the vitreous or subconjunctival. Such injection may suitably be given periodically, depending on the clinical status, once in a every 2 to 6 months.

The term "parenteral" as used herein refers to modes of administration which include intravenous, intramuscular, intraperitoneal, intrastemal, subcutaneous and intrarticular injection and infusion.

In a preferred embodiment, administration is intravenously, intrathecally or via nasal administration (intranasally). Particularly, for the treatment of cerebral edema or in combination therapy of ischemic stroke, preferred administration modes for delivery to vascular bed in the area of the blood brain barrier, is intrathecal or intranasal administration. As used herein, the term "intrathecal administration" includes delivering a PDGF-C antagonist in a pharmaceutical formulation directly into the cerebrospinal fluid of a subject, by techniques including lateral cerebroventricular injection through a burrhole or cisternal into the cisterna magna or lumbar puncture into the lumbar regions or the like, as described, for example, in Lazorthes et al., Advances in Drug Delivery Systems and Applications in Neurosurgery, 143-192, and Omaya et al., Cancer Drug Delivery, 1: 169-179). The term "lumbar region" is intended to include the area between the third and fourth lumbar (lower back) vertebrae. The term "cisterna magna" is intended to include the area where the skull ends and the spinal cord begins at the back of the head. The term "cerebral ventricle" means the cavities in the brain that are continuous with the central canal of the spinal cord. Administration of a PDGF-C antagonist to any of the above mentioned sites can be achieved by direct injection of the PDGF-C antagonist or by the use of infusion pumps.

For injection, the PDGF antagonist formulation of the invention can be formulated in liquid solutions, preferably in physiologically compatible buffers such as Hank's solution or Ringer's solution. In addition, the PDGF antagonist formulation may be formulated in solid form and re-dissolved or suspended immediately prior to use. Lyophilized forms are also included. The injection can be, for example, in the form of a bolus injection or continuous infusion (e.g., using infusion pumps) of the PDGF antagonist formulation.

In one embodiment of the invention, a PDGF antagonist formulation is administered by lateral cerebroventricular injection into the brain of a subject in the inclusive period from the time of the injury for several hours or even days if necessary to reduce the edema in the tissue. The injection can be made, for example, through a burr hole made in the subject's skull. In another embodiment, encapsulated PDGF antagonist may be administered through a surgically inserted shunt into the cerebral ventricle of a subject in the inclusive period from the time of the injury for several hours or even days if necessary to reduce the edema in the tissue. For example, the injection can be made into the lateral ventricles, which are larger, even though injection into the third and fourth smaller ventricles can also be made.

In yet another embodiment, the PDGF antagonist formulation is administered by injection into the cisterna magna, or lumbar area of a subject in the inclusive period from the time of the injury for several hours or even days if necessary to reduce the edema in the tissue.

In a further embodiment, intranasal administration has been verified as a useful mode of administration via a direct nose-brain pathway (Pietrowsky et al., Biol. Psychiatry, 39(5):332-340 (1996), and the PDGF antagonist formulation can be administered in this manner.

The PDGF antagonist is also suitably administered by sustained-release systems. A PDGF antagonist formulation may further be included in a fibrin sealant as described in U.S. Pat. No. 6,117,425. Other suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman et al., Biopolymers 22:547-556 (1983)), poly(2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP 133,988). Sustained-release PDGF antagonist compositions also include lipid entrapped PDGF antagonists, such as liposomes containing PDGF antagonists which are prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type—which the lipid content is greater than about 30 mol. percent cholesterol, the selected proportion being adjusted for the optimal PDGF antagonist therapy.

Preparations of the PDGF antagonists of the present invention should pass the blood-brain barrier (J. Lipid Res., 32, 713-722 (1991)) so that effectiveness to cerebral vascular tissue is ensured in which tPA increases vascular permeability resulting in edema. For this purpose, a liposome preparation may be prepared according (e.g. using a method described in Knight, Liposomes: From Physical Structure to Therapeutic Applications, pages 51-82, Elsevier, Amsterdam, 1981).

When a PDGF antagonist, especially a PDGF-C antagonist, is used in combination with tPA to improve its treatment of ischemic stroke or other situations where thrombolysis is needed, the PDGF antagonists may be administered along with tPA using the same delivery method and routes which most commonly include intravenous reperfusion. Alternatively, as the patient's situation may require, PDGF antagonist may be delivered before, or after tPA treatment, using one of the routes described above.

Typically, tPA is administered as an initial bolus followed by infusion. One of ordinary skills in the art will recognize that the choice of delivery routes depend on the types of the antagonist used. For example, neutralizing antibodies may be delivered directly into the CSF or I.V. For small molecules, such as Gleevec®, it can be delivered through oral administration or directly into the CSF.

PDGF-C agonists would be used to open blood neural barrier—specifically in the blood-brain barrier or retina to deliver therapeutics to the target site. Preferably, the delivery targets the CNS, e.g. via the nasal route, or an invasive neurosurgical approaches (such as into the arterial circulation of the brain, direct injection into the CNS substance or CNS lesions, intraventricular injection, intrathecal drug delivery), or using a devices for drug delivery to the CNS (such as a nanotechnology-based devices and implants for CNS). For improved drug delivery to the CNS across the BNB, the BNB may be further opened via osmotic opening, chemical opening, via cerebral vasodilatation, or with a nitric oxide donor, or via manipulation of the sphingosine 1-phosphate receptor system. Transport across the BNB may further be facilitated pharmacologically, e.g. via modification of the drug to enhance its lipid solubility, transvascular use of transport or carrier systems, use of receptor-mediated transocytosis. Drug delivery to the CNS may further be facilitated by using novel formulations such as crystalline formulations, liposomes, monoclonal antibodies, microspheres, microbeads and lipid-coated microbubble and nanoparticles. Biochip implants, such as controlled-release microchip and retinal implant chip may also be used for drug delivery to the CNS. When delivered systemically, the drug is preferably in a sustained and/or controlled release formulation.

Pharmaceutical Compositions

Another embodiment of the present invention relates to pharmaceutical compositions comprising one or more PDGF antagonists, or one or more PDGF agonists, according to the invention, together with a physiologically- and/or pharmaceutically-acceptable carrier, excipient, or diluent. Physiologically acceptable carriers, excipients, or stabilizers are known to those skilled in the art (see Remington's Pharmaceutical Sciences, 17th edition, (Ed.) A. Osol, Mack Publishing Company, Easton, Pa., 1985). Acceptable carriers, excipients or stabilizers are nontoxic to recipients at the dosages and concentrations employed, and include buffers such as phosphate, citrate, and other organic acids; hydrophobic oils derived from natural or synthetic sources; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The above methods and compositions are especially suitable for use in human treatment. For example, the PDGF-C antagonists may be administered to a stroke patient concurrently or sequentially with tPA. A person of ordinary skills will be able to determine which combination therapy approach, that administering the antagonists before, concurrently, and/or after administration of tPA.

PDGF agonists of the present invention can be used to increase BNB permeability for delivery therapeutic agents for the treatment many disorders of the nervous system, such as Neurodegenerative diseases (Alzheimer's disease, Parkinson's disease, Huntington's disease and Multiple Sclerosis (MS), amyotrophic lateral sclerosis (ALS or Lou Gehrig's Disease)), CNS involvement in Hunter syndrome, mitochondrial encephalopathies, cerebrovascular disease (e.g. stroke; restenosis; cerebral ischemia; intracranial aneurysms, subarachnoid hemorrhage, and vasospasm), psychiatric illness (anxiety, depression, schizophrenia, and sleep disorders), disorders of memory/cognition, epilepsy (e.g. treating with carbamazepine, diazepam); pain (considered to be a neurological disorder); migraine, spasticity (e.g. treatment with intrathecal baclofen), brain tumors (especially malignant gliomas), physical trauma (traumatic brain injury, spinal cord injury and other CNS injury), vasospasm, retinal disorders such as age-related macular degeneration, and CNS infections such as encephalitis and meningitis, and neuroAIDS).

EXAMPLES

Example 1

PDGF-AA, PDGF-BB and PDGF-CC Induce Brain Edema Following Intraventricular Injection Wild type C57BL6 mice (10 Week old) were injected intraventricularly into the dorsal third ventricle with 2 µl of PBS, active PDGF-AA, PDGF-BB (both from Preprotech Inc.) and PDGF-CC (see below) (3 µM). Evans Blue was given intravenously immediately after the injection. One hour after the injection, the animals were perfused with PBS and the brain tissue was removed and processed for Evans Blue extravasation.

As shown in FIG. 1, all three PDGFs, in the CSF, are potent inducers of opening of the BBB.

Example 2

Anti-PDGF-CC Antibodies Blocked PDGF-CC Mediated Activation of PDGFR-α

To monitor growth factor-induced tyrosine phosphorylation of PDGFR-a, serum-starved porcine aortic endothelial (PAE) cells with stable expressing of human PDGFR-α were incubated on ice with 80 µg/ml PDGF-AA, PDGF-BB, or activated PDGF-CC core protein, respectively. The growth factors had prior to addition to the cells been incubated with 3 µg of affinity-purified rabbit polyclonal antibodies against PDGF-CC (rabbit no. 615), or with 3 µg of preimmune rabbit IgG from the same rabbit. The cells were lysed as previously described (Li et al. 2000, Nat. Cell Biol. 2:302-309) and PDGFR-α was immunoprecipitated using a specific antiserum (Eriksson et al. 1992, EMBO J. 11:543-550). Precipitated proteins were subjected to SDS-PAGE under reducing conditions. Tyrosine phosphorylated PDGFR-α was detected by immunoblotting using anti-phosphotyrosine antibodies (PY99, Santa Cruz)

Figure 2:
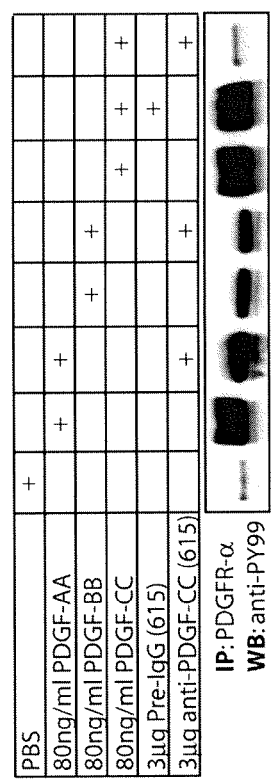
FIG. 2 shows that antibodies to PDGF-CC specifically neutralize the activity of PDGF-CC in ligand-induced activation of PDGFR-α. The PDGFR-α was immunoprecipitated from lysed cells using a specific antibody and activated receptors were visualized using an anti-phosphotyrosine antibody, PY99.

To determine the neutralizing activity of the antibodies to PDGF-CC PAE cells were treated with PDGF-AA, PDGF-BB and PDGF-CC preincubated with affinity-purified antibodies to PDGF-CC, or preincubated with preimmune IgG. The results are shown in FIG. 2, and indicate that the rabbit anti-PDGF-CC antibodies blocked the PDGF-CC mediated activation of PDGFR-α while being unable to do so using PDGF-AA or PDGF-BB as receptor agonists. Preimmune IgG did not affect the ability of PDGF-AA, PDGF-BB or PDGF-CC to efficiently block receptor activation. Thus the antibodies to PDGF-CC are able to specifically neutralize the action of PDGF-CC.

Example 3

Both tPA and PDGF-CC Open the Blood Brain Barrier

Wild type C57BL6 mice (10 Week old) were injected intraventricularly into the dorsal third ventricle with 2 µl of either PBS, wild type murine tPA (3 µM), active PDGF-CC (3 µM), or wild type murine tPA (3 µM) plus active PDGF-CC (3 µM). Evans Blue was given intravenously immediately after the injection. One hour after the injection, the animals were perfused with PBS and the brain tissue was removed and processed for Evans Blue extravasation.

Figure 3:
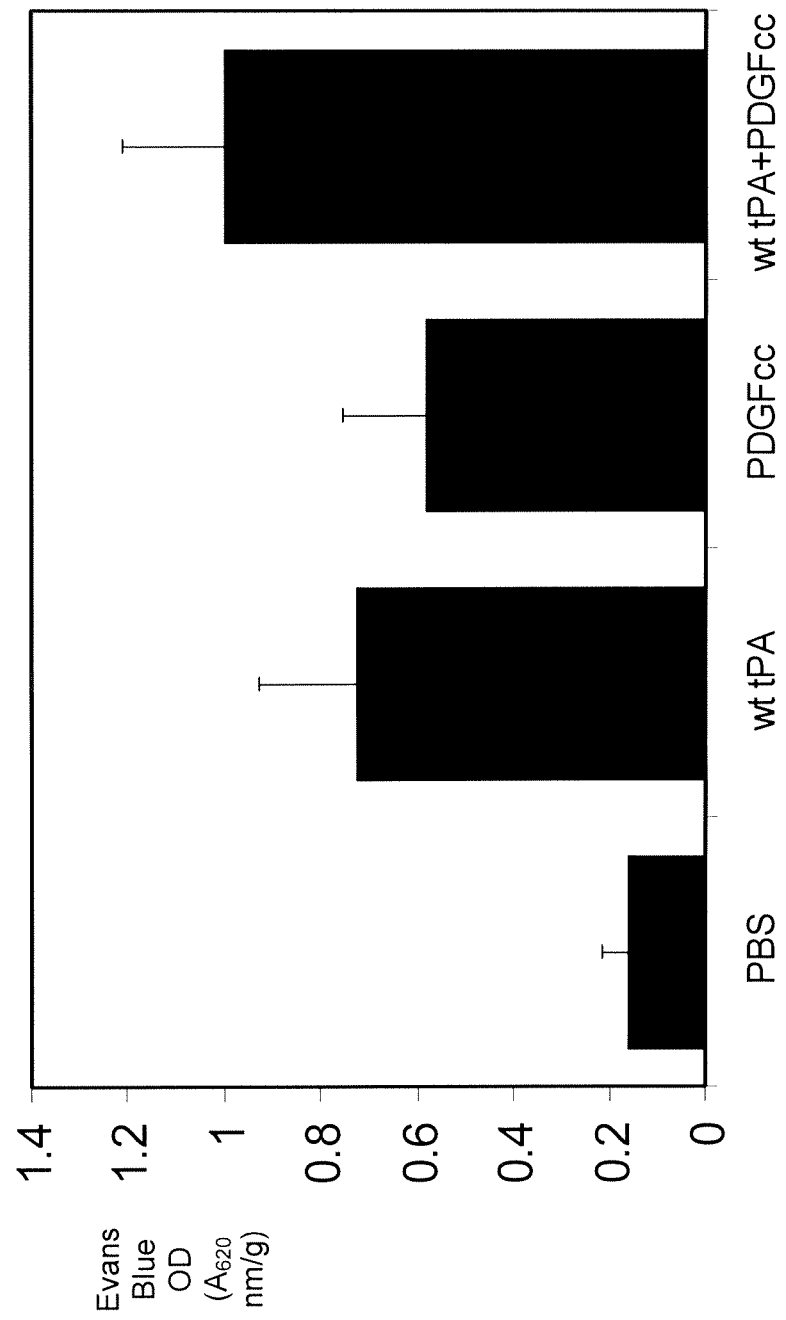
FIG. 3 shows that tPA, as well as PDGF-CC in the CSF, are potent inducers of opening of the BBB, but tPA together with PDGF-CC did not significantly increase BBB opening, suggesting the both tPA and PDGF-CC are able to open the BBB, but the effects are not synergistic or additive.

As shown in FIG. 3, tPA, as well as PDGF-CC in the CSF, are potent inducers of opening of the BBB. However, tPA together with PDGF-CC did not significantly increase BBB opening, suggesting that both tPA and PDGF-CC are able to open the BBB, but the effects are not synergistic or additive.

Example 4

Anti-PDGF-C Antibodies Reduce Evans Blue Extravasation

Wt C57BL6 mice (10 Week old) were injected intraventricularly with 3 µl of either PBS, wild type murine tPA (3 µM), wild type murine tPA (3 µM) with rabbit anti-PDGF-CC (150 µg/ml). Evans Blue was given intravenously immediately after the injection. One hour after the injection, the animals were perfused with PBS and the brain tissue was removed and processed for Evans Blue extravasation.

Figure 4:
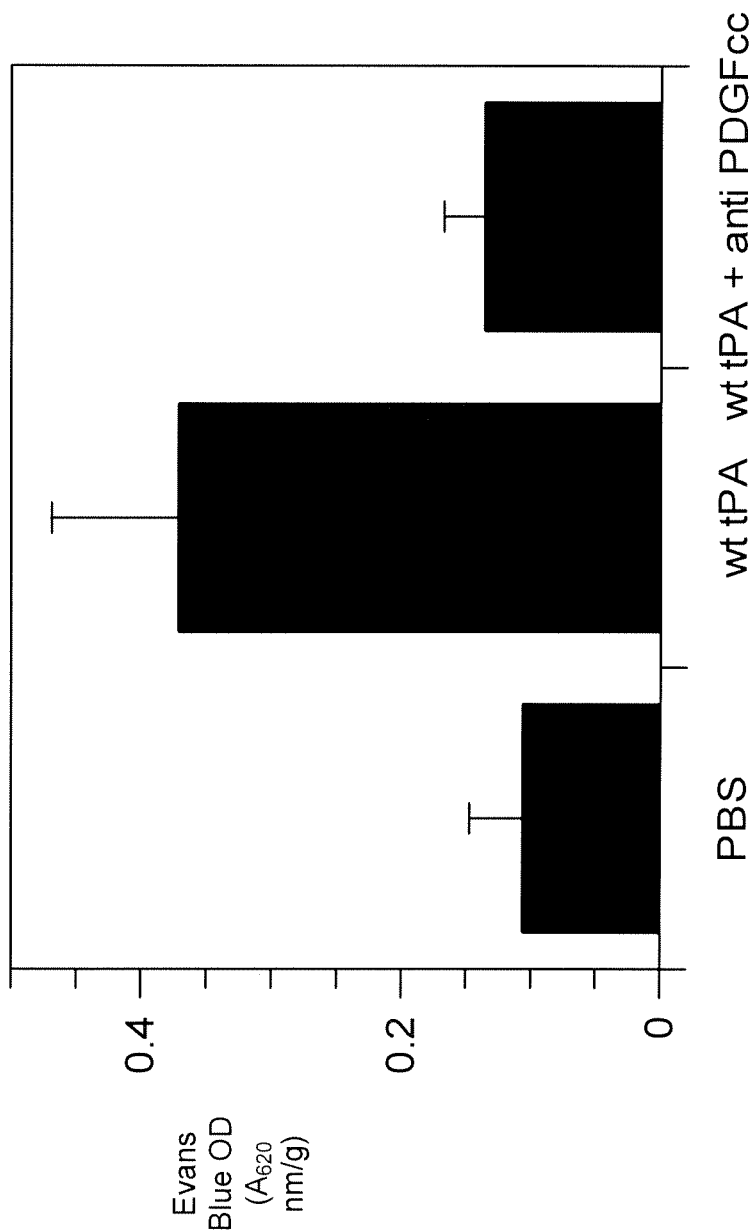
FIG. 4 shows that when tPA was injected together with an anti-PDGF-CC antibody, a dramatic reduction of Evans Blue extravasation was observed, suggesting that tPA regulation of BBB opening involves PDGF-CC.

As shown in FIG. 4, when tPA was injected together with an anti-PDGF-CC antibody, a dramatic reduction of Evans Blue extravasation was observed. This suggests that tPA regulation of BBB opening must involve PDGF-CC, most likely via activating the PDGF-CC from its latent form. Accordingly, PDGF-CC antagonists may be utilized to treat ischemia stroke patients and possibly other patients where cerebral edema is a significant problem. In particular an antagonist of PDGF-CC combined with tPA could be used to extend the therapeutic window of tPA treatment in ischemic stroke, which is currently limited to 3 hour after the onset of symptoms.

Example 5

Injection of PDGF-CC into the CSF Induces Edema

Figure 5:
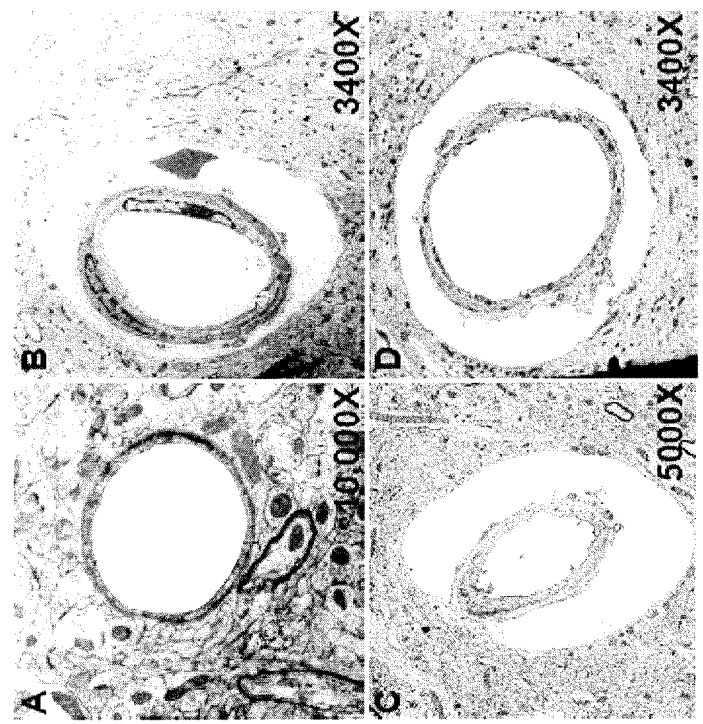
FIG. 5 shows morphological evidence of increased vascular permeability and perivascular edema with PDGF-CC injection to CSF. Electron microscopy of vessels in the brain from mice treated by intraventricular injection 1 hour prior to analysis. Panel A, PBS; panel B, tPA (2 µL at a concentration of a 1 µM); panels C and D PDGF-CC (3 µL at a concentration of a 1 µM). Panels B-D show arterioles surrounded by fluid-filled spaces indicative of developing edema. The approximate magnification is indicated on each panel.

As further evidence that PDGF-CC is a substrate for tPA in the CNS, and mediates tPA's ability to induce increased vascular permeability, we have shown that intraventricular injection of PDGF-CC induces edema. Specifically, tPA or active PDGF-CC (2 µL each at a concentration a 1 µM) were injected intraventricularly into mice, and morphological analysis of the cerebrovascular structure was performed. PBS was used as control. FIG. 5 shows representative transmission electron micrographs of cerebral vessels from the cortex of mice 1 hour after the injection of tPA or PDGF-CC (FIG. 5A, PBS; 5B, tPA (2 µL at a concentration of a 1 µM); 5C and 5D PDGF-CC (2 µL at a concentration of a 1 µM)). FIGS. 5B-D show arterioles surrounded by fluid-filled spaces indicative of developing edema. The approximate magnification is indicated on each panel. As shown in FIGS. 5B and 5D, tPA and PDGF-CC injections induce areas of fluid accumulation surrounding the vessels that likely represent edema formation (i.e. arterioles surrounded by fluid-filled spaces indicative developing edema).

Those data support the conclusion that PDGF-CC acts downstream of tPA, and is a tPA substrate that regulates vascular permeability.

Example 6

PDGF-CC and the PDGFR-α Receptor are Localized to the Neurovascular Unit

Figure 6:
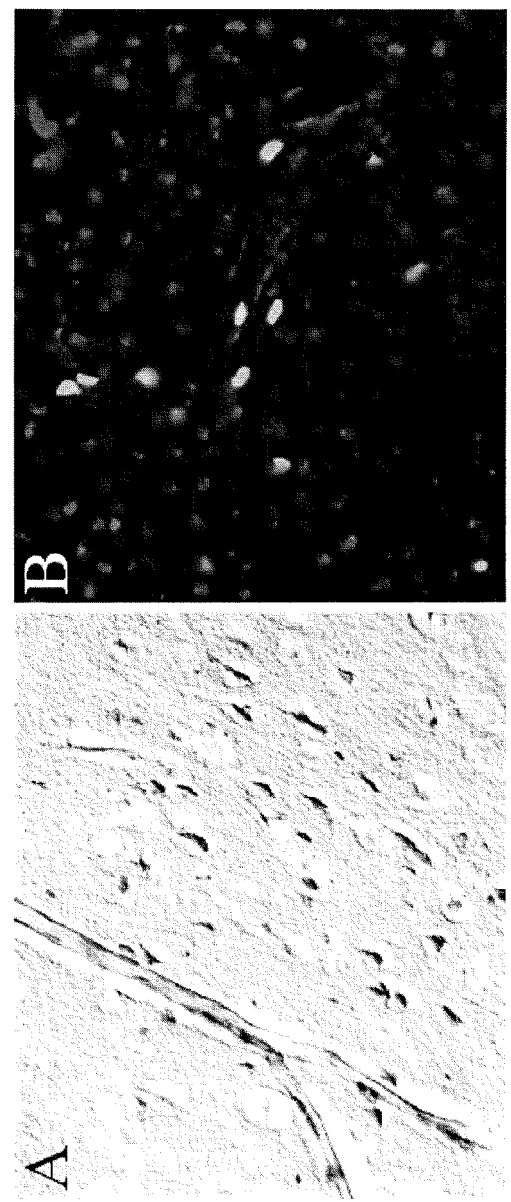
FIG. 6 shows the localization of PDGF-CC and the PDGF a-receptor in the neurovascular unit. Panel A shows PDGF-CC expression in cells associated with cerebral vessels, panel B shows the PDGF α-receptor expression associated with PECAM positive cerebral vessels. In panel A, PDGF-CC expression is detected from β-galactosidase activity in mice heterozygous for β-galactosidase knocked into the PDGF-CC gene (Ding et al. A specific requirement for PDGF-C in palate formation and PDGFR-alpha signaling. Nat Genet. 2004 36:1111-6). In panel B PDGF α-receptor expression is detected in knock-in mice heterozygous for a PDGF α-receptor-GFP chimera (Hamilton et al. Molecular and Cellular Biology, 2003; 23:4013-23). PECAM is detected by immunofluorescence and the nuclei are stained with DAPI.

We have examined the localization of PDGF-CC and the PDGF alpha receptor in the CNS of normal mice. These data are shown in FIG. 6, and they indicate that both PDGF-CC and its alpha receptor are associated with the neurovascular unit.

Panel A shows PDGF-CC expression in cells associated with cerebral vessels, panel B shows the PDGF α-receptor expression associated with PECAM positive cerebral vessels. In panel A, PDGF-CC expression is detected from β-galactosidase activity in mice heterozygous for β-galactosidase knocked into the PDGF-CC gene (Aase et al. Mechanisms of Development 2002; 110:187-91). In panel B PDGF α-receptor expression is detected in knockin mice heterozygous for a PDGF α-receptor-GFP chimera (Hamilton et al. Molecular and Cellular Biology, 2003; 23, 4013-25). PECAM is detected by immunofluorescence and the nuclei are stained with DAPI.

Although the precise cell type has not yet been identified, co-staining with PECAM (FIG. 6B) suggests that the alpha receptor is not associated directly with endothelial cells, but is in cells immediately adjacent to the endothelial cells, possibly smooth muscle cells or perivascular astrocytes.

Example 7

Pharmacologic Inhibition of the PDGF Receptor Reduces Ischemia-Induced Loss of Blood Brain Barrier Integrity and Infarct Volume after Stroke Because PDGF-CC activation may also play a role in regulating cerebrovascular permeability following cerebral ischemia, inhibition of the PDGF receptor may represent a stroke treatment strategy. The photothrombotic stroke model was used to examine the efficacy of a small molecule inhibitor of the PDGF receptor, imatinib mesylate (Gleevec®).

Mice were treated twice daily PO with either Gleevec® or vehicle beginning 12 hours before stroke, and infarct evolution together with cerebrovascular permeability were measured.

Male C57BL/J mice were stroked using photothrombotic method. Gleevec® was given PO twice a day at (600 mg/kg/day) beginning 12 hours before the induction of stroke. Twenty three hours after stroke, animal was given 100 ul of Evans Blue (4%) intravenously. One hour later, the animal was euthanized, perfused with PBS and brain tissue extracted for Evans Blue measurement (n=4-5 for each condition).

Figure 7:
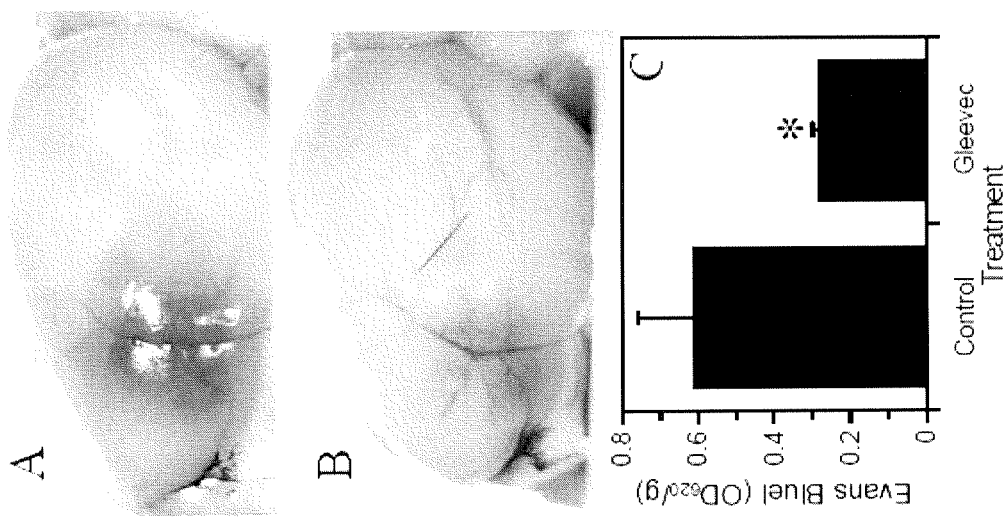
FIG. 7 shows that Gleevec® treatment reduces Evans Blues extravasation after stroke. Male C57BL/J mice were stroked using a photothrombotic method, as described in Nagai et al., Recombinant human microplasmin: production and potential therapeutic properties. J. Thromb. Haemost. 2003 1:307-13m and Nagai et al., Effects of plasminogen activator inhibitor-1 on ischemic brain injury in permanent and thrombotic middle cerebral artery occlusion models in mice. J. Thromb. Haemost. 2005, 3:1379-84. Cerebral blood flow (CBF) was measured using a doppler device. Gleevec® was given PO twice a day at (200 mg/kg/day) beginning 12 hours before the induction of stroke. Twenty three hours after stroke, the animal was given 100 µl of Evans Blue (4%) intravenously. One hour later, the animal was euthanized, perfused with PBS, and brain tissue was extracted for Evans Blue measurement (n=4-5 for each condition and the * indicates p<0.05). Panels A (Control) and B (Gleevec®) show representative images of the ipsilateral hemisphere 24 hours after stroke from animals injected with Evans Blue one hour before euthanasia, panel C shows the quantitation of Evans Blue in the ischemic hemisphere (n=4-5 for each condition and the * indicates p<0.05.
Figure 8:
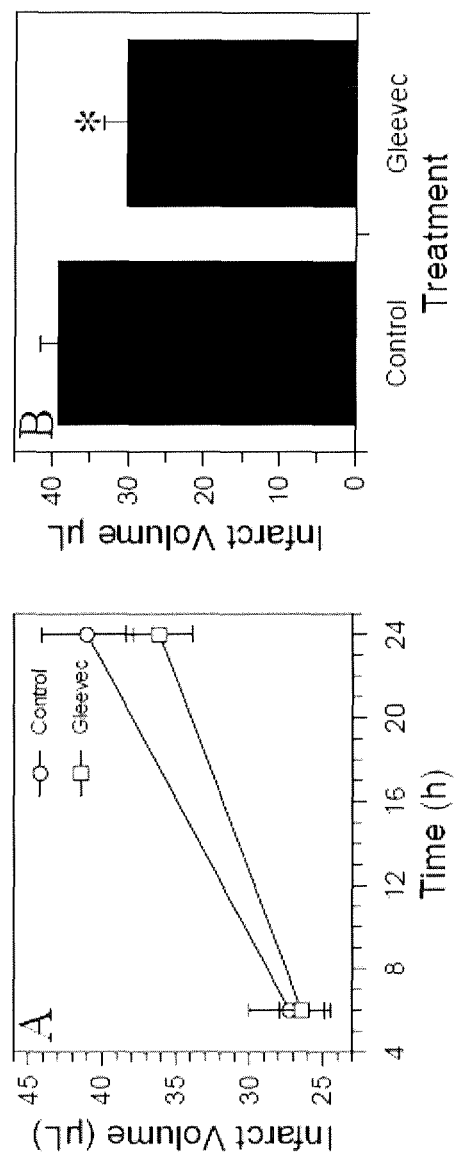
FIG. 8 shows that Gleevec® treatment reduces infarct volume after stroke. Male C57Bl/J (10 week old) were stroked and treated with Gleevec® as described in FIG. 6. Panel A: stroke volume analysis by T2-weighted MRI scan in the same animals 6 hours and 24 hours after stroke. Panel B: stroke volume analysis by TTC staining 72 hours after stroke. For this analysis, animals were euthanized and brains were removed, sliced in 2 mm coronal sections, stained with TTC and stroke volumes were calculated using Image J analysis of TTC stained coronal sections (n=4-8 for each condition and time point and the * indicates p<0.05).

As shown in FIG. 7, Gleevec® treatment significantly (* indicates $p<0.05$) reduced Evans Blue extravasation at 24 hours post stroke, suggesting that PDGF receptor signaling regulates cerebrovascular permeability following cerebral ischemia. Importantly, mice treated with Gleevec® also showed a reduction in stroke volume by T2-weighted MRI at 24 hours but not at 6 hours after stroke induction (FIG. 8A). The difference in stroke volume with Gleevec® treatment was even greater at 72 hours where infarct volume was reduced approximately 25% compared to control mice (FIG. 8B).

Taken together, these data further demonstrate that PDGF-CC is an important substrate for tPA in the neurovascular unit and that it is a significant regulator of cerebrovascular permeability following cerebral ischemia. Furthermore, these data support that small molecule inhibitors of PDGF receptors are suitable for improved treatment for stroke. Gleevec® is especially notably because it is approved, very well tolerated and has a well established safety record. While recent reports suggest that long term use of Gleevec® may lead to cardiac toxicity in some patients, only a short period of treatment is likely needed in the case acute stroke treatment, where toxicity has not been reported.

Example 8

Role of PDGF-CC/tPA in Regulation of the Blood-Retina Barrier

The above data show that tPA-mediated activation of PDGF-CC controls the vascular permeability of a subset of vessels in the brain following ischemic stroke, and that interfering with this signaling mechanism using antibodies to PDGF-CC or a small molecule to PDGFRα greatly reduces edema formation and infarction volume in stroke.

This example shows that both PDGF-CC and the PDGFR-α are expressed in the neurovascular unit of other sites of blood/neural interface, specifically the blood/retina barrier.

Methods:

Retinas from adult C57/bl mice were isolated, and snap frozen and cryosectioned, and postfixed in 4% paraformaldehyde for 10 min. Immunolocalization of endothelial cells using platelet-endothelial cell adhesion molecule (PECAM) as the marker, and astrocytes were identified using glial fibrillary acidic protein (GFAP) as the marker. For PECAM localization, a rat monoclonal antibody was used (BD Pharmingen, dilution 1:100) and secondary antibody anti-Rat-Alexa 594 (Molecular Probes, dilution 1:300). For GFAP localization a rabbit antibody was used antibody (Dako, dilution 1:1000), and secondary antibody anti-rabbit-Alexa 594 (Molecular Probes 1/300). Slides were mounted with Vectashield mounting media for fluorescence containing DAPI (Vector Laboratories). Bound antibodies were visualized using a fluorescence microscope (ZEISS Axiophot).

For immunolocalization of PDGF-CC, isolated eyes were fixed in 4% paraformaldehyde in PBS overnight at 4° C. and processed for paraffin embedding, sectioning, and rehydration. The sections were stained with affinity-purified rabbit anti-PDGF-C antibodies (Li et al. Nat. Cell Biol. 2, 302-309, 2000) using 6 μg of Ig/ml overnight at 4° C. Bound antibodies were visualized using an ABC staining kit (Vector Laboratories), mounted and viewed in a normal light microscope.

For analyses of whole mount adult retina preparation, retinas from heterozygous transgenic mice carrying a mutant allele with a nuclear targeted histon 2B/GFP fusion protein targeted to the PDGFR-α locus (Hamilton et al. Mol Cell Biol. 23, 4013-4025, 2003) were isolated by microdissection, immunostained and processed for confocal microscopy essentially as described (Gerhart et al. J. Cell Biol. 161: 1163-1177, 2003). Primary antibodies were anti-PECAM (as above, BD Pharmingen), or anti-NG2 (Chemicon) to visualize pericytes. Expression of PDGFR-α was determined by GFP fluorescence. Fluorescence images were taken by a fluorescence microscope.

Figure 9:
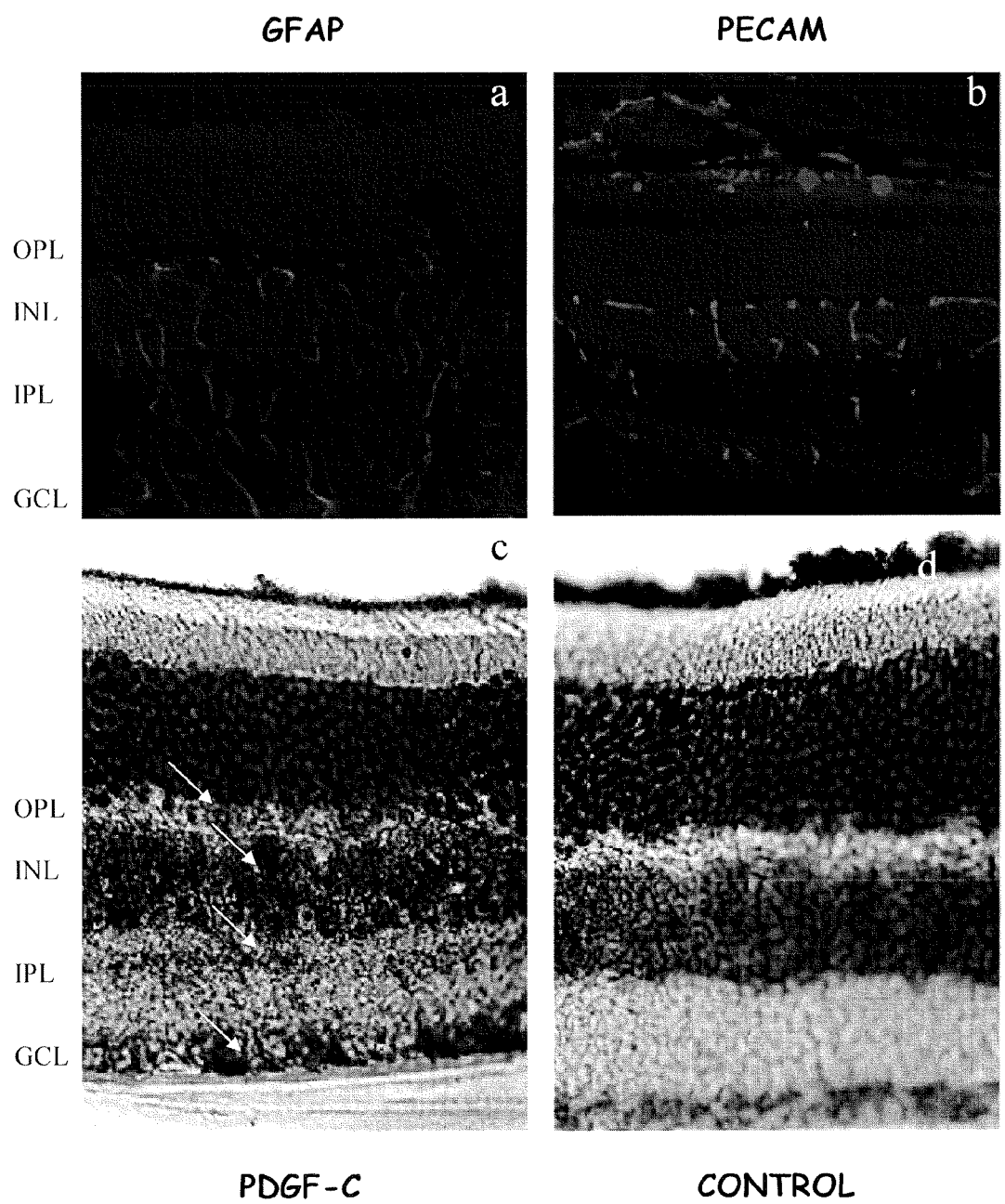
FIG. 9 shows the immunolocalization of astrocytes (a), endothelial cells (b), and PDGF-CC in adult mouse retina. PDGF-CC was most abundant in OPL, INL, IPL, and GCL (FIG. 9c). Staining with control Ig gave only background staining (FIG. 9d).

Results:

Immunocalization of GFAP and PECAM revealed that both astrocytes and blood vessels, respectively, were particularly abundant in outer plexiform layer (OPL), inner nuclear layer (INL), inner plexiform layer (IPL), and in the ganglion cell layer (GCL) (FIGS. 9a and 9b). PDGF-CC was most abundant in OPL, INL, IPL, and GCL (FIG. 9c). Staining with control Ig gave only background staining (FIG. 9d). Thus PDGF-CC was expressed in the same compartment of the retina as the perivascular astrocytes and the blood vessels.

The results show that PDGF-CC (visualized by the red-brownish staining color) is expressed in outer plexiform layer, in the inner nuclear layer, in the inner plexiform layer and in the ganglion cell layer similar to the marker for astrocytes and endothelial cells.

Figure 10:
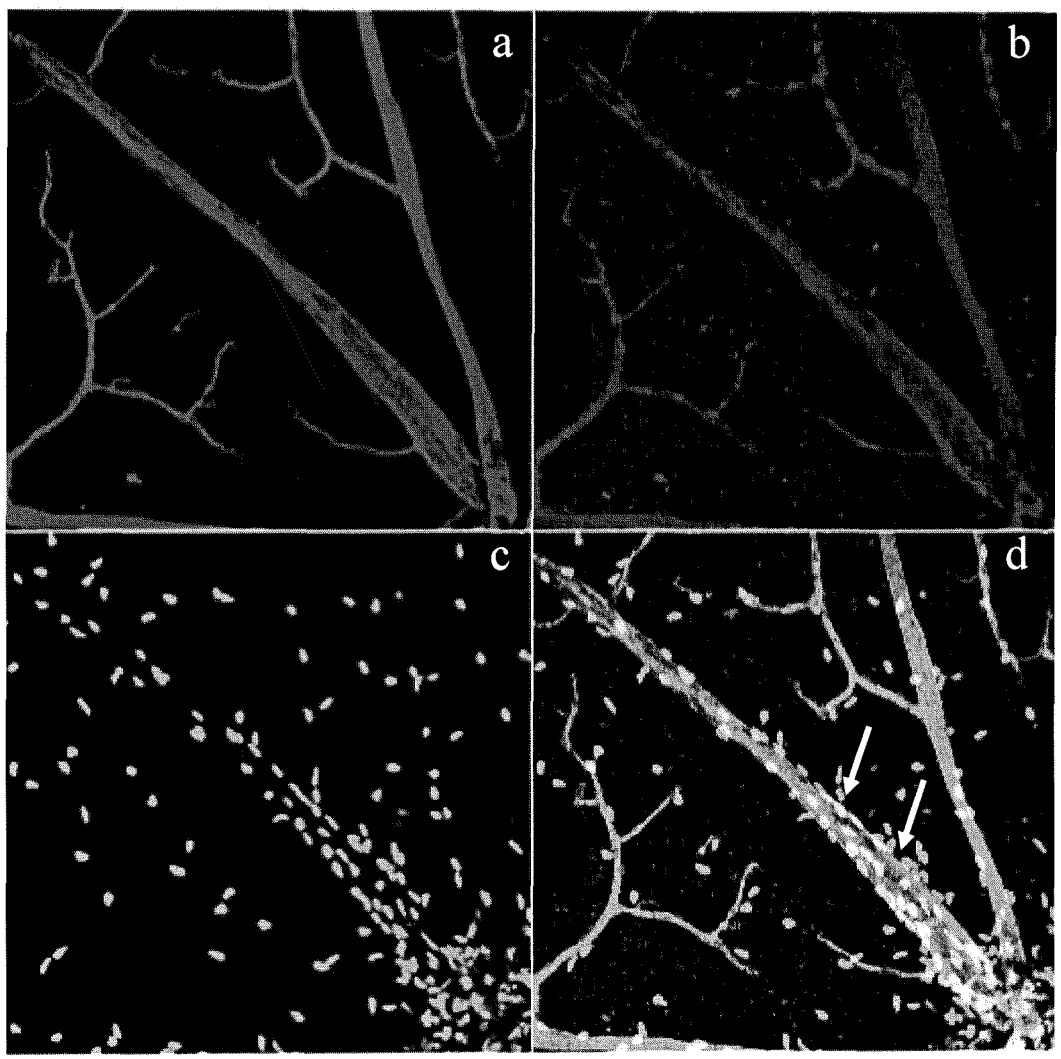
FIG. 10 shows the results of immunofluorescence localization of GFP-PDGFRα-expressing cells in adult mouse retina. Blood vessels were localized using PECAM as the marker (a), and pericytes were localized using NG2 as the marker (b). PDGFRα expression was localized using a nuclear targeted histone 2B/GFP fusion protein knocked into the PDGFRα locus (green nuclei, but as white dots on dark background in (c)). The overlay of a-c shows that GFP-expressing cells are closely attached to smaller arteries and arteriolas ((d), white arrows).

To localize the expression of PDGFRα in adult mouse retina we determined the localization of GFP using retinas from a transgenic mouse strain expressing the fluorescent protein under the endogenous control elements. The results showed that GFP expression is particularly abundant in small arteries and arteriolas of the retinal vasculature (FIG. 10). The GFP expressing cells are probably perivascular astrocytes. Thus the neurovascular units in brain and retina vasculatures are very similar suggesting that vascular permeability in the brain and retina is regulated using a common mechanism, namely tPA-mediated activation of PDGF-CC.

The results of immunofluorescence localization of PDGFRα-expressing cells in adult mouse retina are shown in FIG. 10. Blood vessels were localized using PECAM as the marker (a), and pericytes were localized using NG2 as the marker (b). PDGFRα expression was localized using a nuclear targeted histone 2B/GFP fusion protein knocked into the PDGFRα locus (green nuclei in c). The overlay of a-c shows that GFP-expressing cells are closely attached to smaller arteries and arteriolas (d, white arrows). No obvious association between the GFP expressing cells and smaller vessels were observed.

With these experiments we have shown that PDGF-CC and its signaling receptor PDGFRα are expressed in or close to the neurovascular unit of the retinal vasculature. Together with previous knowledge, this information provides evidence for a role of tPA-mediated activation of PDGF-CC as a major factor regulating blood vessel permeability in the retina similar to our observations in brain. Since retinal vessel permeability and edema formation in the retina are common causes of visual impairment and even blindness, these results indicate that by inferring with PDGF-CC signaling in retina it may be possible to reduce or remove edema formation in the retina.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof. All references cited hereinabove and/or listed below are hereby expressly incorporated by reference.

What is claimed is:

1. A method for treating neural edema in a higher vertebrate animal in need of such treatment comprising administering to said animal an effective amount of an anti-PDGF-CC antibody or an anti-PDGF-C antibody.

2. The method of claim 1 wherein the animal is a mammal.

3. The method of claim 1 wherein the animal is a human.

4. The method of claim 1 wherein the antibody is a monoclonal antibody.

5. The method of claim 1 wherein the antibody is a chimeric, humanized or fully-human antibody.

6. The method of claim 1 wherein the antibody is administered intravenously.

7. The method of claim 1 wherein the antibody is delivered by injection.

8. The method of claim 1 wherein the neural edema is associated with administration of tissue-type plasminogen activator (tPA).

9. The method of claim 8 wherein the anti-PDGF-CC antibody binds specifically to the tPA proteolytic site of PDGF-CC.

10. A method for treating stroke in a higher vertebrate animal suffering from stroke comprising administering to said animal an effective amount of an anti-PDGF-CC antibody or an anti-PDGF-C antibody in combination with tissue-type plasminogen activator (tPA).

11. The method of claim 10 wherein the animal is a mammal.

12. The method of claim 10 wherein the animal is a human.

13. The method of claim 10 wherein the antibody is a monoclonal antibody.

14. The method of claim 10 wherein the antibody is a chimeric, humanized or fully-human antibody.

15. The method of claim 10 wherein the antibody is administered intravenously.

16. The method of claim 10 wherein the antibody is delivered by injection.

17. The method of claim 10 wherein the antibody and tPA are administered concurrently.

18. The method of claim 10 wherein the antibody and tPA are administered sequentially.

19. The method of claim 18 wherein the antibody is administered before tPA is administered.

20. The method of claim 18 wherein the antibody is administered after tPA is administered.

21. The method of claim 10 wherein the stroke is ischemic stroke.

\* \* \* \* \*